(12) United States Patent
Bryland et al.

(10) Patent No.: US 10,004,762 B2
(45) Date of Patent: Jun. 26, 2018

(54) DIALYSIS FORMULATION

(71) Applicant: Gambro Lundia AB, Lund (SE)

(72) Inventors: Anna Bryland, Lomma (SE); Ola Carlsson, Lund (SE); Karin Sandin, Södra Sandby (SE)

(73) Assignee: GAMBRO LUNDIA AB, Lund (SE)

( * ) Notice: Subject to any disclaimer, the term of this patent is extended or adjusted under 35 U.S.C. 154(b) by 0 days. days.

(21) Appl. No.: 14/787,293

(22) PCT Filed: May 8, 2014

(86) PCT No.: PCT/EP2014/059471
§ 371 (c)(1),
(2) Date: Oct. 27, 2015

(87) PCT Pub. No.: WO2014/180959
PCT Pub. Date: Nov. 13, 2014

(65) Prior Publication Data
US 2016/0067278 A1 Mar. 10, 2016

(30) Foreign Application Priority Data

May 8, 2013 (SE) ...................................... 1350573
May 8, 2013 (SE) ...................................... 1350574

(51) Int. Cl.
*A61K 31/194* (2006.01)
*A61K 33/00* (2006.01)
(Continued)

(52) U.S. Cl.
CPC ............ *A61K 33/00* (2013.01); *A61K 31/194* (2013.01); *A61K 33/04* (2013.01); *A61K 33/08* (2013.01);
(Continued)

(58) Field of Classification Search
CPC .. A61K 2300/00; A61K 31/194; A61K 33/00; A61K 33/04; A61K 33/08;
(Continued)

(56) References Cited

U.S. PATENT DOCUMENTS 5,102,910 A * 4/1992 Mittheiss ............. A61K 31/315
424/641
5,108,767 A 4/1992 Mulchandani et al.
(Continued)

FOREIGN PATENT DOCUMENTS

EP 2039758 3/2009
JP 2001513370 9/2001
(Continued)

OTHER PUBLICATIONS

Allain et al. (Abstract of: Presse Med 1984;13(37):2249-51).*
(Continued)

*Primary Examiner* — Ernst V Arnold
(74) *Attorney, Agent, or Firm* — K&L Gates LLP

(57) ABSTRACT

The invention relates to a dialysis formulation, optionally a citrate containing dialysis formulation, comprising selenium (Se), optionally in combination with further trace elements selected from rubidium (Rb), cobalt (Co), molybdenum (Mo), and zinc (Zn). The dialysis formulation is intended to be used in dialysis treatment.

9 Claims, 10 Drawing Sheets

(51) Int. Cl.
  A61K 33/04  (2006.01)
  A61K 33/08  (2006.01)
  A61K 33/24  (2006.01)
  A61K 33/30  (2006.01)
  A61K 33/32  (2006.01)
  A61K 33/34  (2006.01)

(52) U.S. Cl.
  CPC ............. *A61K 33/24* (2013.01); *A61K 33/30* (2013.01); *A61K 33/32* (2013.01); *A61K 33/34* (2013.01)

(58) Field of Classification Search
  CPC ........ A61K 33/24; A61K 33/30; A61K 33/32; A61K 33/34
  See application file for complete search history.

(56) References Cited

U.S. PATENT DOCUMENTS

| | | | |
|---|---|---|---|
| 5,728,678 | A | 3/1998 | Trimbo et al. |
| 2004/0060865 | A1 | 4/2004 | Callan et al. |
| 2004/0253323 | A1 | 12/2004 | Giles |
| 2005/0100613 | A1 | 5/2005 | Giordano et al. |
| 2005/0260277 | A1 | 11/2005 | Giles |
| 2006/0078629 | A1* | 4/2006 | Serfontein ............ A23L 33/165 424/702 |
| 2008/0015487 | A1 | 1/2008 | Szamosfalvi et al. |
| 2008/0131525 | A1 | 6/2008 | Heyland |
| 2009/0045121 | A1 | 2/2009 | Kabayama et al. |
| 2009/0074883 | A1* | 3/2009 | Gupta ..................... A23L 1/302 424/643 |
| 2010/0187476 | A1 | 7/2010 | Yugari et al. |
| 2011/0065808 | A1 | 3/2011 | Yamamoto et al. |
| 2012/0265116 | A1 | 10/2012 | Szamosfalvi et al. |

FOREIGN PATENT DOCUMENTS

| | | |
|---|---|---|
| JP | 2007-056013 | 3/2007 |
| WO | WO997419 | 2/1999 |
| WO | 01015745 | 3/2001 |
| WO | 2010112538 | 10/2010 |
| WO | 2011161055 | 12/2011 |
| WO | 2011161056 | 12/2011 |
| WO | 2014058329 | 4/2014 |

OTHER PUBLICATIONS

Remington: The Science and Practice of Pharmacy 2006 pp. 802 and 837; 3 pages.*
Skipton et al., Drinking Water: Bacteria 2014; 5 pages.*
Haas et al. Staying Healthy with Nutrition, rev: The complete guide to diet and nutritional medicine. 2012 pp. 223-224; 1 page (Year: 2012).*
Rydon R. Profiles of the Nutrients 2. Minerals and Trace Elements. 2017 p. 98; 1 page (Year: 2017).*
Cardarelli (Materials Handbook: A Concise Desktop Reference) 2013 pp. 91-92). (Year: 2013).*
Barany et al., "Inductively Coupled Plasma Mass Spectrometry for Direct Multi-element Analysis of Diluted Human Blood and Serum," Journal of Analytical Atomic Spectrometry, Sep. 1997, vol. 12 (1005-1009).
Boosalis et al., "The Role of Selenium in Chronic Disease," Nutrition in Clinical Practice, vol. 23, No. 2, Apr./May 2008, 152-160.
Bryland, et al., "Citate treatment reduces endothelial death and inflammation under hyperglycaemic conditions," Diabetes & Vascular Disease Research, 9(1) 42-51.
Canavese et al., "Rubidium deficiency in dialysis patients," Journal of Nephrology, May-Jun. 2001, vol. 14, No. 3, pp. 169-175.
Canavese et al., "Rubidium, Salami and Depression," Blood Purif, 2008;26:311-314, 2008.
Cefalu et al., "Role of Chromium in Human Health and in Diabetes," Diabetes Care, vol. 27, No. 11, Nov. 2004, pp. 2741-2751.
Ciechanover et al., "Malrecognition of Taste in Uremia," Nephron 26: 20-22 (1980).
Druml et al., "Parenteral nutrition in patients with renal failure—guidelines on Parenteral Nutrition, Chapter 17," German Medical Science 2009, vol. 7, p. Doc11.
Dursun et al., "Are Uremia, Diabetes, and Atherosclerosis Linked With Impaired Antioxidant Mechanisms?" Journal of Investigative Medicine 56(2):545-552, 2008.
Faure et al., "Selenium supplementation decreases nuclear factor-kappa B activity in peripheral blood mononuclear cells from type 2 diabetic patients," European Journal of Clinical Investigation (2004) 34, 475-481.
Hsieh et al., "Long-Term Changes in Trace Elements in Patients Undergoing Chronic Hemodialysis," Biological Trace Element Research, 2006, 109(2): p. 115-21.
International Search Report for International Application No. PCT/EP2014/059471, mailed Jul. 8, 2014.
Kalantar-Zadeh et al., "Malnutrition-Inflammation Complex Syndrome in Dialysis Patients: Causes and Consequences," American Journal of Kidney Diseases, vol. 42, No. 5 Nov. 2003; pp. 864-881.
Kashiwagi et al., "Abnormal glutathione metabolism and increased cytotoxicity caused by H2O2 in human umbilical vein endothelial cells cultured in high glucose medium," Diabetologia (1994) 37: 264-269.
Lapolla et al., "Pentosidine Plasma Levels and Relation with Metabolic Control in Diabetic Patients," Horm Metab Res 2005; 37: 252-256.
Lynch et al., "Altered Taste Perception and Nutritional Status Among Hemodialysis Patients," Journal of Renal Nutrition, 2012: pp. 1-8.
Marques de Mattos et al., "Protein Oxidative Stress and Dyslipidemia in Dialysis Patients," Therapeutic Apheresis and Dialysis 2012; 16(1):68-74.
Mekki et al., "Hemodialysis duration impairs food intake and nutritional parameters in chronic kidney disease patients," Int Urol Nephrol (2012) 44:237-244.
Morales et al., "Pentosidina: un nuevo biomarcador de las complicaciones en la diabetes mellitus," Med Clin (Barc). 2011:136(7):298-302. Translation of Abstract Only.
Relman, "The Physiological Behavior of Subidium and Cesium in Relation to That of Potassium," Yale J biol Med, 1956, 29(3): p. 248-62.44(1): p. 237-44.
Richard et al., "Reversal of selenium and zinc deficiencies in chronic hemodialysis patients by intravenous sodium selenite and zinc gluconate supplementation. Time-course of glutathione peroxidase repletion and lipid peroxidation decrease," Biological Trace Element Research Nov.-Dec. 1993, vol. 38,No. 2-3, pp. 149-159.
Rucker et al., "Trace Element Status in Hemodialysis Patients," Seminars in Dialysis—vol. 23, No. 4 Jul.-Aug. 2010 pp. 389-395.
Sabbioni et al., "Salts as a source of metals in dialysis fluids; an assessment study by means of neutron activation analysis" 1989 The Science of the Total Environment, 84, 13-23.
Sjöberg et al., "Pentraxin 3, a Sensitive Early Marker of Hemodialysis-Induced Inflammation," Blood Purif 2012;34:290-297.
Sprenger et al., "Improvement of uremic neuropathy and hypogeusia by dialysate zinc supplementation: A double-blind study," Kidney International, vol. 24, Suppl. 16 (1983), pp. S-315-S-318.
Tanaka et al., "Role of Copper Ion in the Pathogenesis of Type 2 Diabetes," Endocrine Journal 2009, 56 (5), 699-706.
Temple et al., "Selenate-Supplemented Nutritional Formula Increases Plasma Selenium in Hemodialysis Patients Address wprinr quests to," Journal of Renal Nutrition, vol. 10, No. 1, Jan. 1, 2000, pp. 16-23.
Tonelli et al., "Trace elements in hemodialysis patients: a systematic review and meta-analysis," BMC Medicine, Biomed Central Ltd., London, vol. 7, No. 1, May 19, 2009, p. 25.
Vanholder et al., "The role of trace elements in uraemic toxicity," Nephrol Dial Transplant (2002) 17 [Suppl 2]: 2-8.

(56) References Cited

OTHER PUBLICATIONS

Wu et al., "Urinary 8-OHdG: a marker of oxidative stress to DNA and a risk factor for cancer, atherosclerosis and liabetics," Clinica Chimica Acta 339 (2004) 1-9.
Zima et al., "Trace Elements in End-Stage Renal Disease," Blood Purif 1999; 17:187-198.
Guan et al., "Clinical Blood Purification," Shandong Science and Technology Press, Nov. 2003 (p. 69, paras. 3-4).
State Intellectual Property Office of the People'S Republic of China, English Translation of Third Office Action for Chinese Patent Application No. 201480001556.0 (related to above-captioned patent application), dated May 9, 2017.
English Translation of Office Action issued in related Japanese Patent Application No. 2016-512382, dated January 17, 2018.
Japanese Journal of Hygiene, 2009, vol. 64, No. 2, p. 431.
Krizek, M., et al., "Influence of Hemodialysis of Selenium Blood Levels," Sbornik lekarsky, vol. 101 (2000) No. 3, p. 241-248.
Padovese, P., et al., "Trace Elements in Dialysis Fluids and Assessment of the Exposure of Patients on Regular Hemodialysis, Hemofiltration and Continuous Ambulatory Peritoneal Dialysis," Nephron 1992;61:442-448.

\* cited by examiner

DIALYSIS FORMULATION

PRIORITY CLAIM

This application is a 371 National Stage Application of International Application No. PCT/EP2014/059471, filed May 8, 2014, which claims priority to and the benefit of Swedish Application No. 1350573-0, filed May 8, 2013, and claims priority to and the benefit of Swedish Application No. 1350574-8, filed May 8, 2013, the disclosures of each of which are incorporated by reference herein in their entireties.

TECHNICAL FIELD

The present invention relates to a dialysis formulation comprising one or more trace elements. Also, the present invention relates to a citrate containing dialysis formulation comprising one or more trace elements. The dialysis formulation may be used in extracorporeal blood treatments, such as intermittent and continuous dialysis treatment, as well as peritoneal dialysis treatment.

BACKGROUND OF THE INVENTION

The present invention relates to a composition, a dialysis formulation, comprising trace elements. Especially, the dialysis formulation comprises selenium. The dialysis formulations are intended for dialysis treatment.

Dialysis is a well-established treatment technique for patients having kidney malfunction. The dialysis treatment artificially replaces some of the functions of the kidney. The dialysis treatment may be of different kinds, such as hemodialysis (intermittent or continuous) or peritoneal dialysis.

During dialysis treatment the blood is forwarded to a dialyzer (or filter, etc) and uremic toxins in the blood are removed. However, also the levels of other components in the blood are affected by the dialysis treatment. Trace elements are a group of essential substances that are present in minute quantities in the human body necessary for life. They have the capability to work both as antioxidants by being a co-factor, or being a part of essential enzymes, or by being able to induce oxidative stress by their chemical properties.

Regarding trace elements there are no general principles of how they are affected by dialysis therapy. Studies have shown that some trace elements, like chromium, copper and manganese are higher in dialysis patients, pre-dialysis compared to healthy subjects, due to ureamic conditions. Dialysis treatment is not efficient in respect of these trace elements and the levels of the trace elements are therefore raised. For some other trace elements are there indications that the levels instead are decreased, both pre-dialysis and during dialysis treatment. In addition, even if some trace element levels rise or decrease during a dialysis treatment, are the start level (pre-dialysis) often altered (higher or lower) compared with a healthy person, due to decreased or increased removal over time.

Zima, T. et al., Blood Purif 1999; 17:187-198, 'Trace Elements in End-Stage Renal Disease', indicates that the amount of trace elements may change during dialysis treatment. Regarding selenium, it is herein described that selenium deficiency is to be suspected and supplementation may thereof be beneficial.

Tonelli, M. et al., BMC Medicine 2009, 7:25, 'Trace elements in hemodialysis patients: a systemic review and meta-analysis.' describes that the level of the trace elements selenium, zinc, and manganese is lower in patients undergoing haemodialysis treatment when compared with normal and healthy control species. Herein it is also indicated that the dialysate concentration of trace elements are routinely not measured and/or manipulated.

Also Gidden, H. et al., Trans Am Soc Artif Intern Organs 1980; Vol XXVI, 133-138, describes the change of trace elements during dialysis treatment. The movement of the trace elements are described to depend on the metal-protein binding constant.

Cano, N. J. M., et al., Clinical Nutrition 28 (2009) 401-414, *ESPEN Guidelines on Parenteral Nutrition: Adult Renal Failure', and Singer, P., et al., Clinical Nutrition 28 (2009) 387-400, 'ESPEN Guidelines on Parenteral Nutrition: Intensive Care' provide guidelines on parenteral nutrition to be applied in adult renal failure and intensive care, respectively. Micronutrients like trace elements are added to nutrient mixtures for parenteral administration.

US 2008/0015487 describe dialysis fluids comprising trace elements. However, this document only describes presence of trace elements in general in dialysis fluids. There is no indication that there is a need to be selective in the administration of trace elements to the dialysis patient.

There are no dialysis products available where it is possible to be selective in the choice of trace element. There are products for i.v. infusion available on the market containing a palette of trace elements, for example Tracel® and Decan®. Tracel® contains $Cr^{3+}$, $Cu^{2+}$, $Fe^{3+}$, $Mn^{2+}$, $Zn^{2+}$, $F^-$, $I^-$, $MoO_4^{2-}$, and $SeO_3^{2-}$ (according to its Summary Product Characteristics, SPC). In a similar way, the Decan® contains Fe, Zn, Cu, Mn, F, Co, I, Se, Mo, and Cr (according to its SPC). However, these trace elements are always delivered in combinations of trace elements to the subject in need thereof. According to the SPC's for those two products, there is a need to investigate the blood levels of manganese during long time use, i.e. more than four weeks.

Selenase® is a solution comprising selenium in form of selenite. It is intended to be used via infusion or injection to patients having selenium deficiency.

There is a need to replace the selenium when deficiency of selenium occurs. Especially, there is a need to replace selenium lost during the dialysis treatment and there is a need for formulations for dialysis treatment comprising selenium.

There are dialysis fluids available suitable for profiling or manipulation of different components removed or decreased in amount during dialysis. However, there are no dialysis products available where it is possible to be selective in the choice of trace element.

The purpose of the invention illustrated herein is to maintain physiological level of the trace elements which are decreased during the dialysis treatment. It has been shown that some trace elements are decreasing during dialysis treatment, while the level of some others are left unchanged, and some others are increasing or accumulated during the dialysis treatment.

Therefore, with the trace element containing products available today there is no possibility to replace individual trace elements, for example the trace elements that are lost during the dialysis treatment.

With a dialysis formulation comprising selenium and, optionally rubidium it is possible to manipulate and make sure that a proper dosage of those trace elements is given.

SUMMARY OF THE INVENTION

One object of the present invention is to provide a composition, a dialysis formulation, comprising selenium (Se).

In one embodiment the dialysis formulation comprises selenium (Se), wherein the formulation contains selenium in a concentration of 0.5-2.5 μM of selenium (Se), preferably 0.6-1.8 μM of selenium (Se), and more preferably 1-1.5 μM of selenium.

The selenium may be in form of selenite ($SeO_3^2 \times H_2O$).

The advantage of this embodiment is that the dialysis formulation may provide selective replacement of selenium. By such replacement it may be possible to reduce the effects of deficiency of selenium, such as occurrence of oxidative stress and inflammation which is induced by uremic condition and dialysis treatment. Oxidative stress and inflammation play a crucial role in the development of cardiovascular disease and atherosclerosis enhanced by dialysis treatment.

Another embodiment of the invention is the dialysis formulation comprising selenium (Se) as above, with the proviso that the dialysis formulation is essentially free of one or more of the trace elements selected from chromium (Cr), manganese (Mn), and copper (Cu).

The advantage of this embodiment is that the dialysis formulation may provide selective replacement of selenium. By such replacement it may be possible to reduce the effects of deficiency of selenium, such as occurrence of oxidative stress and inflammation which is induced by uremic condition and dialysis treatment. Oxidative stress and inflammation play a crucial role in the development of cardiovascular disease and atherosclerosis enhanced by dialysis treatment. A further embodiment of the invention is a dialysis formulation being a citrate containing dialysis formulation comprising the trace element selenium (Se).

Another embodiment of the invention is a dialysis formulation according to any of the embodiments above wherein the dialysis formulation further comprises one or more trace elements selected from the group of cobalt (Co), molybdenum (Mo), and zinc (Zn).

By the present dialysis formulation it is possible to keep further trace elements on a physiologically acceptable level.

In another embodiment is a dialysis formulation, according to any of embodiments described above, which further comprises rubidium (Rb) provided. The dialysis formulation may contain between 0.1-4.7 μM rubidium (Rb), preferably between 1.4-4.2 μM rubidium (Rb), more preferably 1.6-2.5 μM rubidium. For example, the dialysis formulation contains 0.1-2.7 μM rubidium (Rb), or between 1.4-2.7 μM rubidium (Rb).

In another embodiment of the invention, the dialysis formulation as described above is a treatment fluid to be used in dialysis treatment. Further, the dialysis formulation may be a dialysis fluid. It may also be a replacement fluid.

The dialysis formulation may also be a peritoneal dialysis fluid.

The dialysis formulation as defined may be used in dialysis treatment of a diabetic patient.

Another embodiment of the invention is the dialysis formulation as above for dialysis treatment. The dialysis treatment may be intermittent dialysis treatment. Alternatively, the dialysis treatment may be continuous dialysis treatment; or the treatment may be peritoneal dialysis treatment.

Another embodiment of the present invention is the trace element Selenium for use in dialysis therapy.

Another embodiment is the dialysis formulation according to the above for use in dialysis therapy. Also, an embodiment of the invention is the use of selenium for the manufacturing of a medicament for treatment or prevention of selenium deficiency in connection with dialysis therapy, optionally with the proviso that the medicament is essential free from one or more of chromium (Cr), manganese (Mn), or copper (Cu).

Also, the use of selenium in accordance with the above may further comprise rubidium (Rb).

Another embodiment of the invention is that the dialysis formulation further comprises one or more trace elements selected from the group of cobalt (Co), molybdenum (Mo), and zinc (Zn).

By the dialysis formulation comprising selenium in combination with rubidium it is provided an efficient way to keep the levels of these trace elements at physiologically preferably levels in dialysis patients. In one embodiment the dialysis formulation is a treatment fluid to be used in dialysis treatment. For example, the treatment fluid may be used as dialysis fluid or replacement fluid. In one embodiment of the invention a dialysis formulation comprising the trace element selenium (Se) for dialysis treatment is provided.

The dialysis treatment may be intermittent dialysis treatment; continuous dialysis treatment; or peritoneal dialysis treatment. The intermittent dialysis treatment can be treatments like hemodialysis, hemofiltration, and hemodiafiltration. Another embodiment is provided wherein the dialysis formulation is for continuous dialysis treatment, like CRRT. Another embodiment is provided wherein said dialysis formulation is for peritoneal dialysis treatment. In one embodiment of the invention use of the dialysis formulation comprising selenium in dialysis treatment of diabetic patient is provided. There is an advantage to avoid selenium deficiency in diabetic hemodialysis (HD) patients as they have an increased risk of oxidative stress, inflammation and development of atherosclerosis due to diabetic complications such as hyperglycemia, insulin resistance and formation of advanced glycation end products (AGE). Uremia and hyperglycemia found in this patient population can lead to AGE formation and a significant correlation can be found between high levels of plasma pentosidine, low residual renal function, malnutrition and inflammation. Because this population is already more exposed to potential oxidative stress and inflammation, it is important to be extra observant when managing the trace element status in this patient group. In addition, a significant correlation between low plasma selenium and increased markers for oxidative stress has been found.

In one embodiment use of selenium for the manufacturing of a citrate containing medicament for treatment or prevention of selenium deficiency in connection with dialysis therapy is provided. The medicament is a formulation for dialysis treatment.

In one embodiment a use of the citrate containing formulation is provided. Especially the use is in dialysis treatment of diabetic patients. Diabetic hemodialysis (HD) patients have an increased risk of oxidative stress, inflammation and development of atherosclerosis due to diabetic complications such as hyperglycemia, insulin resistance and formation of advanced glycation end products (AGE). Uremia and hyperglycemia found in this patient population can lead to AGE formation and significant correlation can be found between high levels of plasma pentosidine, low residual renal function, malnutrition and inflammation. Because this population is already more exposed to potential oxidative stress and inflammation, it is important to be extra observant when manage the trace element status in this patient group. In addition, a significant correlation between low plasma selenium and increased levels of markers for oxidative stress has also been found.

BRIEF DESCRIPTION OF THE DRAWINGS

FIG. 3A, PTX-3: FIG. 3B, 8-OHdG: FIG. 3C).

DEFINITIONS

Figure 1:
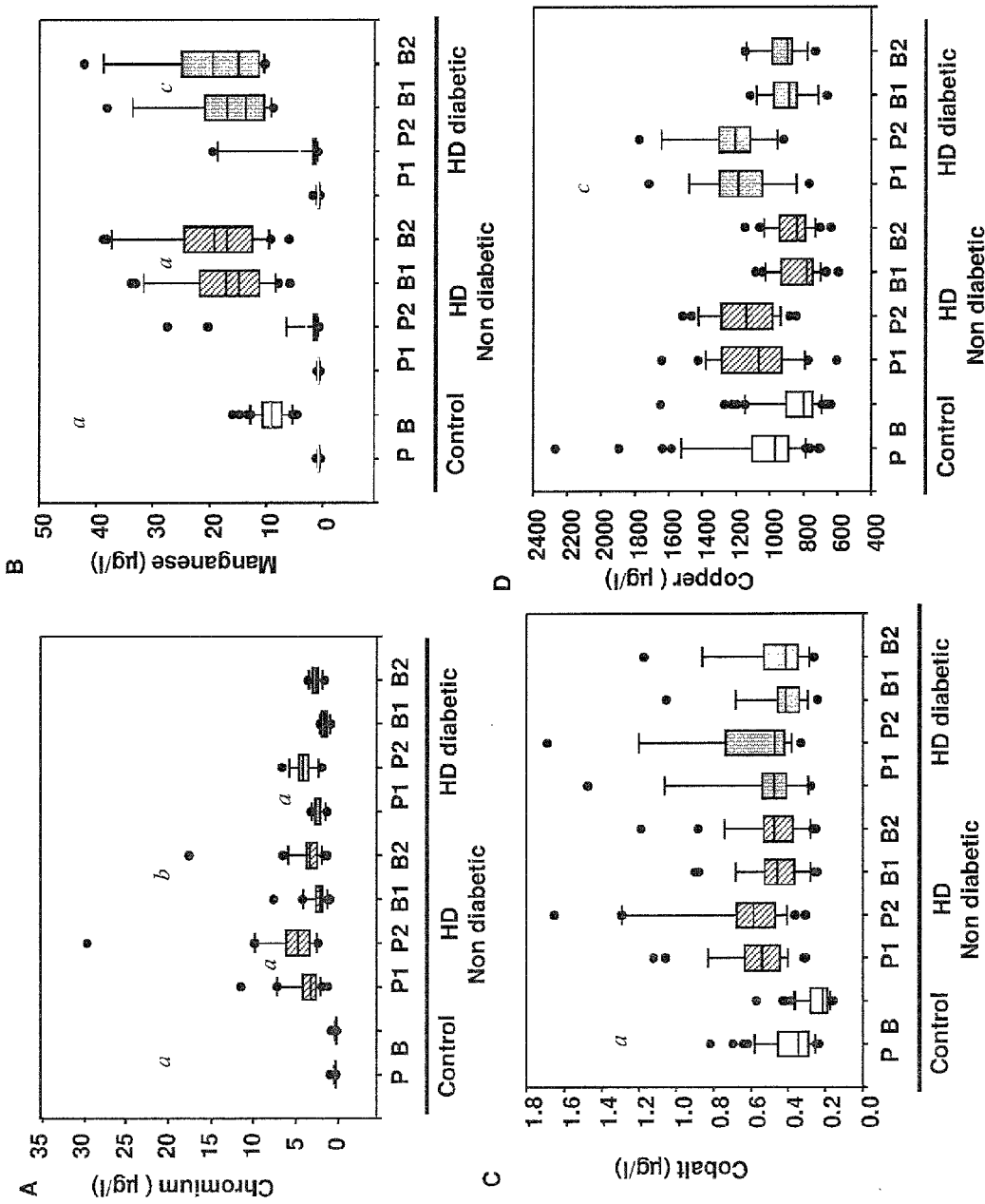
FIG. 1: A-H shows the different levels of trace elements in blood and plasma of HD dialysis patients, non-diabetic and diabetic, and a healthy control group.
Figure 1:
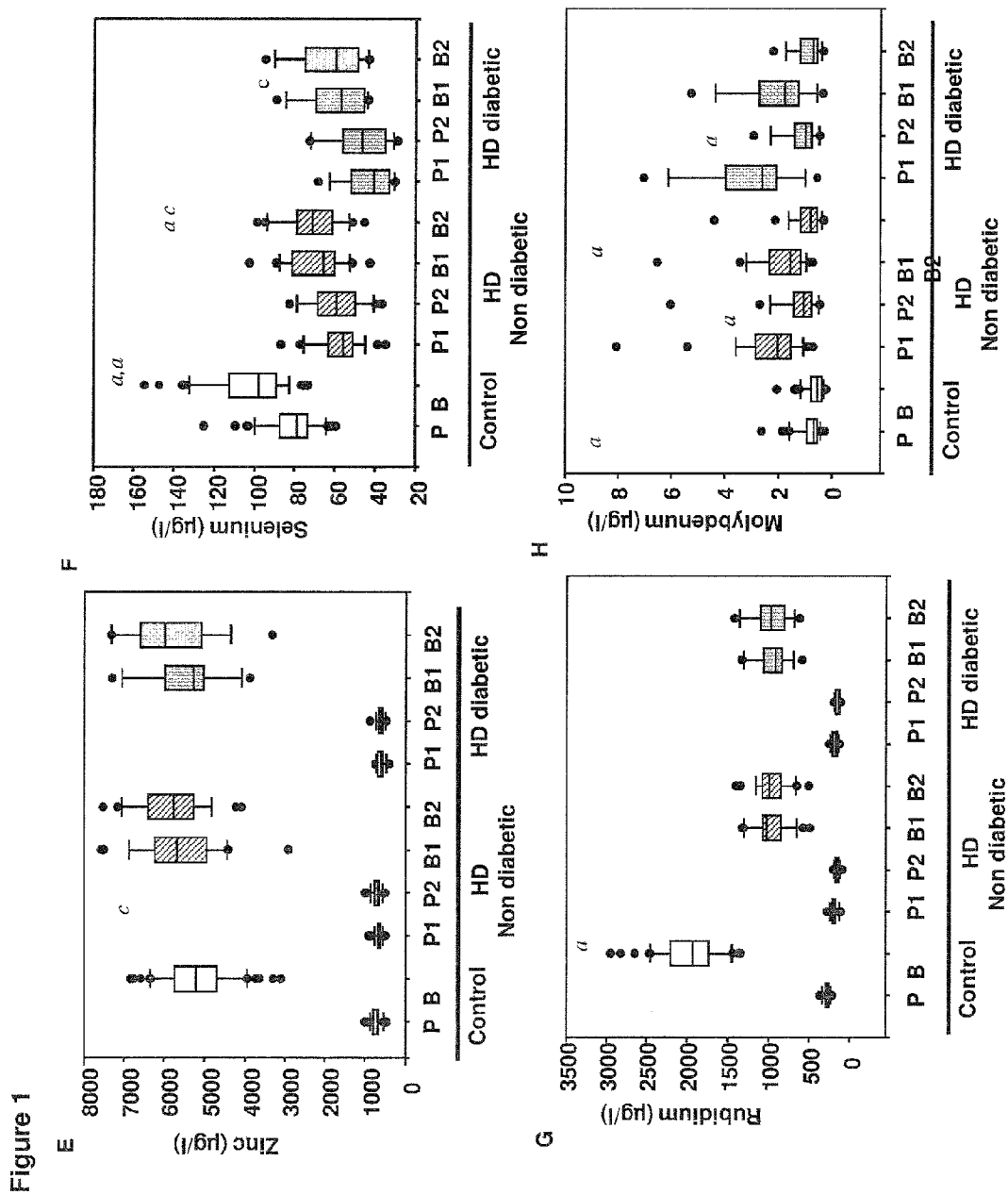

The term "dialysis therapy" or "dialysis treatment" means all types of dialysis therapies or treatments both for chronic renal insufficiency and acute renal insufficiency. Also liver dialysis is included in the term.

The term "CRRT" means a continuous renal replacement therapy and this type of treatment mode is used in case of acute renal insufficiency or in case of chronic renal insufficiency.

By the term "filter" it is herein meant a unit comprising semipermeable membranes. This unit may also be called a semipermeable membrane, a dialyzer, a dialysis filter or a dialysis membrane.

By the term "dialysis formulation" it is herein meant a ready for use formulation, or a pre-formulation which upon preparation results in a ready for use formulation.

The term 'anticoagulation fluid' means a fluid which is intended to provide for the anticoagulation effect within the extracorporeal blood circuit and which is intended to be infused within the extracorporeal blood circuit.

The term "treatment fluid" means a dialysis fluid for perfusion of a filter or an infusion fluid, i.e. a fluid for pre- or postdilution. Thus, treatment fluids include dialysis fluid, infusion fluid, replacement fluid and substitution fluid.

The term "dialysis fluid" means a fluid for perfusion of a filter, on the dialysate side of such a filter, opposite the blood side.

The term "replacement fluid" means a fluid which is infused into the extracorporeal blood circuit either for pre-dilution (pre-infusion), i.e. infused into the extracorporeal blood flow before the blood enters the filter, or for postdilution (post-infusion), i.e. infused into the extracorporeal blood flow after the blood has exited the filter and before the blood is returned to the patient. Replacement fluids are normally also named as infusion fluids, substitution fluids or hemofiltration fluids.

The term 'citrate' means herein citric acid or any salt thereof. The salt may be formed with sodium, magnesium, or potassium, or other physiologically acceptable ions. The sodium citrate may be present as trisodium citrate, disodium hydrogen citrate, or monosodium dihydrogen citrate. The citrate may be added to the anticoagulation fluid and/or the at least one treatment fluid. The term "citrate (total)" means the total amount of citrate present in a fluid, thus representing the sum of citrate in all different forms mentioned above The term "phosphate" means phosphoric acid or any salt thereof. The salt may be formed with sodium, magnesium, potassium, or other physiologically acceptable ions. The component may be added as phosphate ($PO_4^{3-}$), hydrogenphosphate ($HPO_4^{2-}$), or dihydrogen phosphate ($H_2PO_4^{-}$). Examples of salts are trisodium phosphate disodium hydrogenphosphate, monosodium dihydrogen phosphate. The total amount phosphate thus represents the sum of phosphate in all different forms mentioned above.

The term "essentially free from" means that no specific addition as active ingredient or excipient of the component in question has been done.

The term 'selenium' means any physiologically acceptable form of selenium suitable for the purpose.

The term 'rubidium' means any physiologically acceptable form of rubidium suitable for the purpose.

The term 'zinc' means any physiologically acceptable form of zinc suitable for the purpose.

The term 'cobalt' means any physiologically acceptable form of cobalt suitable for the purpose.

The term 'molybdenum' means any physiologically acceptable form of molybdenum suitable for the purpose.

If not otherwise specified, the terms selenium, Se, rubidium, Rb, cobolt, Co, molybdenum, Mb, zinc, Zn, chromium, Cr, manganese, Mn, and, copper, Cu, means the ionic form(s), or salt forms, of that particular trace elements.

DETAILED DESCRIPTION OF THE INVENTION

Selenium (Se) is an essential trace element in the human body. Selenium is, among other things, located at the active site of glutathione peroxidase, which is essential for the cells transformation of hydrogen peroxide to water. Thus, selenium has an important role in reducing oxidative stress.

Severe selenium deficiency may cause or lead to sudden death and cardiomyopathy in the general population. In cases of less severe selenium deficiency there is a problem of hypertension, heart failure, and coronary disease within the general population. In dialysis patients there is a risk for cardiomyopathy. Mild selenium deficiency is linked to reduced oxidative defence and may be susceptibility to oxidative stress. The risk for oxidative stress has been shown to be markedly increased amongst dialysis patients. Therefore, there is an objective to administer selenium during the dialysis treatment.

Trace elements are involved in the oxidative status in different ways, both upon formation of reactive oxygen species (ROS) and in the reduction of ROS. For example chromium and copper have an effect to increase or facilitate ROS formation when being present in excess, but on the other hand are Zn—Cu superoxide dismutase (Zn—Cu SOD) an important antioxidant located in the cytosol. Chromium is also necessary in glucose metabolism. Furthermore, selenium has an effect to decrease the formation of ROS, by its location at the active site of glutathione peroxidase.

Therefore it is important to be selective in the administration of trace elements to the patient undergoing dialysis treatment.

Selenium may be included in the dialysis formulation in the form of selenium oxide, in anhydrous form or in form of hydrate ($SeO_3^{2-} \times nH_2O$).

The ready to use composition of the dialysis formulation contains selenium in an amount of between 0.5-2.5 µM of selenium (Se), preferably 0.6-1.8 µM of selenium (Se), preferably in an amount of 1-1.6 µM. For example in a concentration of a concentration between 1-1.5 µM of selenium, or between 1.1-1.4 µM. For example, the ready for use dialysis formulation comprises 0.6, 0.7, 0.8, 0.9, 1.0, 1.1, 1.2, 1.3, 1.4, 1.5, 1.6, 1.7 or 1.8 µM of selenium.

The dialysis formulation may also, in addition to selenium, also comprise rubidium (Rb). Rubidium may be selected from RbCl, $Rb_2CO_3$, RbOH, $Rb_3PO_4$, or $RbH_2PO_4$. The list is not exhaustive. The dialysis formulation may comprise rubidium in an amount to provide of between 0.1-4.7 µM rubidium (Rb) in the ready-to-use formulation, preferably between 0.1-2.7 µM rubidium (Rb), more preferably between 1.4-2.7 µM rubidium (Rb), and even more preferably 1.6-2.5 µM rubidium, for example in an amount of 1.6-1.9 µM. For example, the citrate containing dialysis formulation contains 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, or 4.2 µM rubidium.

In addition to selenium, and the optionally rubidium, the dialysis formulation may also contain one or more additional trace elements selected from cobalt (Co), molybdenum (Mo), and zinc (Zn). Cobalt may be present in an amount of 0-0.02 µM. Molybdenum may be present in an amount of 0-0.02 µM. Zinc may be present in an amount of 0-11 µM, preferably between 0.15-8 µM, and more preferably between 0.3-8 µM. For example the dialysis formulation may comprise 0-0.76 µM zinc, such as between 0.3-0.6 µM.

Selenium may also be included in the dialysis formulation being a citrate containing dialysis formulation. The form of selenium may be in form or selenium oxide, in anhydrous form or in form of hydrate ($SeO_3^{2-} \times nH_2O$). The dialysis formulation ready to use contains selenium in an amount of 0.6-1.8 µM, preferably in an amount of 1-1.6 µM, and more preferably in an amount of 1.1-1.4 µM. For example, the citrate containing dialysis formulation comprises 0.6, 0.7, 0.8, 0.9, 1.0, 1.1, 1.2, 1.3, 1.4, 1.5, 1.6, 1.7 or 1.8 µM of selenium.

Also, the citrate containing dialysis formulation may also, in addition to selenium, also comprise rubidium (Rb). Rubidium may be selected from the group of RbCl, $Rb_2CO_3$, RbOH, $Rb_3PO_4$, or $RbH_2PO_4$. The list is not exhaustive. The dialysis formulation may comprise rubidium in an amount of 0.1-4.7 µM, The concentration can be 1.4-4.2 µM, preferably in an amount of 1.6-2.5 µM, more preferably in an amount of 1.6-1.9 µM. For example, the citrate containing dialysis formulation contains 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, or 4.2 µM rubidium.

In addition to selenium, and the optionally rubidium, the dialysis formulation may also contain one or more additional trace elements selected from cobalt (Co), molybdenum (Mo), and zinc (Zn). Cobalt may be present in an amount of 0-0.02 µM. Molybdenum may be present in an amount of 0-0.02 µM in the dialysis formulation to be used in dialysis treatment. Zinc may be present in an amount of 0-63 µM. For example in a concentration of between 0-11 µM, preferably between 0.15-8 µM, and more preferably between 0.3-8 µM. For example the dialysis formulation may comprise 0-0.76 µM zinc, such as between 0.3-0.6 µM.

The dialysis formulation may also comprise copper, Cu. The dialysis formulation may comprise copper in a concentration of 0-15.7 µM, for example in a concentration of 6.2-15.7 µM.

Rubidium deficiency is connected to protein malnutrition and inflammation. Non-treated uremic patients often suffer from rubidium deficiency further enhanced by the dialysis treatment, depleting up to 50% of the tissue and blood rubidium concentrations. Rubidium deficiency is linked to protein malnutrition which results in inflammation and depression. Treatment with rubidium chloride has been shown to improve depression by increasing the synaptic neuro-transmitter levels in the central nervous system (CNS) and by that increase dopamine and norepinephrine concentrations. Previously rubidium chloride was sold as an antidepressive drug under the name of Rubinorm.

Zinc (Zn), as a part of Zn—Cu superoxide dismutase, is an important antioxidant, but this ion is also involved in the sense of smell and taste, which, in turn, is correlated to malnutrition.

Cobalt (Co) is a part of the essential vitamin $B_{12}$ (Cobalamin) and is thus involved in the regulation of central nervous system and in the synthesis of erythrocytes. Deficiency can lead to anemia and neurological symptoms due to inhibition of DNA synthesis (Tonelli at al.)

Molybdenum (Mo) is important by being part of varies enzymes active site and there are at least 50 molybdenum containing enzymes in our system.

The dialysis formulation may comprise, in addition to the trace elements as are listed above, suitable active ingredients, excipients and diluents. Examples are electrolytes, water, physiologically acceptable acids, physiologically acceptable bases, amino acids, lipids, etc. In one embodiment, a composition consisting of sodium selenite pentahydrate, sodium chloride, hydrochloric acid and water is disclaimed from the scope of dialysis formulations comprising selenium.

The citrate containing dialysis formulation may comprise, in addition to the trace elements as are listed above, suitable active ingredients, excipients and diluents. Examples are electrolytes, water, physiologically acceptable acids, physiologically acceptable bases, amino acids, lipids, etc.

The citrate containing dialysis formulation may be used in dialysis treatment.

Some of the trace elements are bound to protein with rather high affinity. However, the affinity may change due to changes of the proteins' environment and surroundings. Proteins are in general not able to pass the dialyse membrane placed in the filter. Further, it is known that citrate is able to form complex with some cations, like multivalent cations, for example calcium. Therefore, when using citrate containing formulations in acute dialysis treatment, like continuous dialysis treatment (also called Continuous Renal Replacement Therapy (CRRT)) it is important to compensate for the losses of trace elements caused by the presence of citrate.

Citrate may be present in the dialysis formulation for dialysis treatment for a couple of reasons or purposes. First, the dialysis formulation may comprise citrate for its purpose as an acid to provide a mean to adjust the pH of the composition, to be used in the dialysis treatment or in the dialysis system.

Citrate also has anticoagulation properties, if the fluid containing sodium citrate and/or citric acid is infused close to the blood access where the blood exits the patient and enters into the extracorporeal blood circuit. Citrate acts as an anticoagulation agent by binding to the ionized calcium within the plasma, through calcium citrate complex formation. Ionized calcium is essential for the blood coagulation cascade. The blood coagulation cascade is prevented if the ionized calcium concentration is lowered well below 0.5 mM. To be able to achieve anticoagulation a concentration of about 2-4 mM citrate in the blood entering the dialysis filter is usually sufficient. Citrate that exists in the blood is rapidly metabolized in number of organs, forming close to three bicarbonate ions per citrate ion. As the citrate concentration is lowered in the metabolism, citrate complex bound calcium is released and returned to ionized calcium.

Combining positively charged trace elements, as for example, but not limited to; zinc, cobalt, or rubidium with citrate makes it necessary to make certain adjustments of the composition, since addition of those trace elements will result in complex binding with citrate. Due to the small amounts of trace elements, as well as the high affinity for binding to citrate most of the positively charged trace elements will be complex bound to citrate. This will in turn lead to that the losses of trace elements across the dialysis membrane will be comparable with the amounts of citrate usually lost this way. This result in about 50% loss of positively charged trace elements loss, given in the anticoagulation fluid.

On the other hand if the dialysis solution also contains trace elements, but no citrate, there will be new equilibriums as the dialysis fluid pass across the dialysis membrane. This will result in a transport of trace elements from dialysis fluid to the blood since the concentration of non-bound trace element will be higher on the dialysis side than on the blood side. In total there will be a loss of trace elements that has to be compensated, mainly due to changes in the protein binding of the trace elements.

Since proteins in plasma usually has a negative net charge there is an affinity for positively charged ions on proteins. This will of course also have an impact on the trace element equilibrium across the dialysis membrane since most of the proteins are unable to pass the dialysis membrane.

The final adjustment of trace elements may be done via the post-replacement fluid, if such fluids are used. To avoid that the content of trace elements are limiting the infusion speed it is advisable to have the desired plasma concentration, of course corrected for the amount of protein binding.

When it comes to positively charged trace elements in excess in the circulation of a patient treated with citrate anticoagulation dialysis there may be two different scenarios. Starting with if the positively charged trace elements exists in a free form in the circulation, or if they are bound to other species with a lower or comparable affinity, compared to the affinity to citrate. Then it would be considerable losses of those species via the loss of citrate across the dialysis membrane. On the other hand, if the trace element is protein bound to a major extent, then there will only be a limited removal due to citrate binding and loss of citrate bound trace elements. This may, however, be modified if the amount of trace element bound to proteins are influenced by the citrate binding. Then will the part bound to proteins decrease and bind to citrate instead, and it is possible to reduce the plasma content with dialysis, and thereby, get rid of unwanted trace elements, as well as trace elements in excess from the circulation.

Dialysis is a well-established treatment technique for patients having kidney malfunction. The dialysis treatment artificially replaces the functions of the kidney. There are different types of dialysis treatments, like extracorporeal blood treatments, such as intermittent, continuous, and peritoneal dialysis treatment.

The intermittent dialysis treatment is in the following further described. Examples of intermittent dialysis treatments are hemodialysis, hemofiltration, and hemodiafiltration.

Hemodialysis involves withdrawing blood from the body and cleaning it in an extracorporeal blood circuit and then returning the cleansed blood to the body. The extracorporeal blood circuit includes a filter which comprises a semipermeable membrane. The semipermeable membrane has a blood side and a dialysate side, and waste substances and excess fluid are removed from the blood passing on the blood side of the semipermeable membrane through the semipermeable membrane over to the dialysate side of the semipermeable membrane.

Hemodialysis may be performed in three different treatment modes, hemodialysis, hemofiltration, and hemodiafiltration. Common to all three treatment modes is that the patient is connected by a blood line to the dialysis machine, which continuously withdraws blood from the patient. The blood is then brought in contact with the blood side of the semipermeable membrane within the dialyzer in a flowing manner.

In hemodialysis, an aqueous solution called dialysis fluid is brought in contact with the opposite membrane surface, the dialysate side, in a countercurrent flowing manner. Waste substances (toxins) and solutes are removed/controlled mainly by diffusion. Excess fluid is removed by applying transmembrane pressure over the semipermeable membrane that will cause convective transport of solutes as well. Solutes and nutrients may diffuse in the opposite direction from the dialysis fluid, through the semipermeable membrane and into the blood.

In hemofiltration, no dialysis fluid is brought in contact with the dialysate side of the semipermeable membrane. Instead only a transmembrane pressure is applied over the semipermeable membrane thereby removing fluid and waste substances, from the blood through the semipermeable membrane wall and into the dialysate side thereof (convective flow). Fluid and waste substances are then passed to drain. To replace some of the removed fluid, a correctly balanced electrolyte/buffer dialysis fluid (also named infusion fluid or replacement fluid) is infused into the extracorporeal blood circuit. This infusion may be done either upstream the dialyzer (pre-infusion mode) or downstream the dialyzer (post-infusion mode) or both.

Hemodiafiltration is a combination of hemodialysis and hemofiltration, a treatment mode that combines transport of waste substances and excess fluids through the semipermeable wall by both diffusion and convection. Thus, here a dialysis fluid is brought in contact with the dialysate side of the semipermeable membrane in a continuously flowing manner, and a dialysis fluid (also named infusion fluid or replacement fluid) is used for infusion into the extracorporeal blood circuit in pre-infusion mode, post-infusion mode or both.

For many patients, hemodialysis is performed for 3-5 hours, three times per week. It is usually performed at a dialysis center, although home dialysis is also possible. When home dialysis is performed patients are free to perform dialysis more frequently and also in more gentle treatments with longer treatment times, i.e. 4-8 hours per treatment and 5-7 treatments per week. The dose and treatment times may be adjusted due to different demand of the patients.

In the case of patients suffering from acute renal insufficiency, a continuous treatment, throughout a major portion of the entire day for up to several weeks, a continuous renal replacement therapy (CRRT), or intermittent renal replacement therapy (IRRT) is the indicated treatment depending on the patients status. Also here the removal of waste substances and excess fluid from the patient is effected by any or a combination of the treatment modes hemodialysis, hemofiltration and hemodiafiltration.

All the different treatment described above makes use of a filter and are often called dialysis. A conventional filter comprises a first and a second compartment separated by a membrane, the first compartment having an inlet and an outlet for the circulation of blood there through and the second compartment having an outlet for draining a liquid (e.g. plasma water, plasma, used dialysis liquid). In case the treatment (e.g. hemodialysis) requires the circulation of a treatment liquid (e.g. a dialysis liquid) the second compartment also has an inlet.

In the above treatments, blood is entering the dialysis machine, flown through the first compartment of the filter, and returned to the patient. This part is the so called extracorporeal circuit. In case excess water is to be withdrawn from the blood, this is done across the membrane. In hemodialysis, a dialysis liquid is simultaneously flown through the second compartment of the filter and the metabolic wastes contained in the blood migrate by diffusion through the membrane into the second compartment. In hemofiltration, a pressure difference is created across the membrane so that plasma water flows through the membrane into the second compartment. Metabolic wastes migrate by convection into the second compartment. In order to compensate for the loss of body fluid, the patient is simultaneously infused with a sterile substitution solution. Hemodiafiltration is a combination of hemodialysis and hemofiltration. In this treatment a dialysis liquid is flown through the second compartment and a substitution solution is infused into the patient. In plasmapheresis, a pressure difference is created across the membrane so that plasma (i.e. plasma water and proteins) flows through the membrane into the second compartment. Once treated, the plasma is returned to the patient.

An alternative dialysis treatment to the extracorporeal blood treatments is the peritoneal dialysis treatment. During peritoneal dialysis a fluid containing electrolytes and some kind of osmotic agent, i.e. glucose, amino acids, or glucose polymers, are introduced into the peritoneal cavity via a catheter. The fluid is allowed to equilibrate with the surrounding tissue and its blood vessel system. This results in a removal of fluid and waste products when the fluids are removed from the peritoneal cavity via the catheter. The drainage is usually directly followed by infusion of another portion of peritoneal dialysis fluid. Each cycle is usually lasting for approximately 4-12 hours. Since the removal of fluid and solutes are driven by diffusion and convection there will also be significant losses of other substances. Losses of those from the patient's blood may be undesirable and requires replacement i.e. trace elements.

It is well known that even large molecules are removed via the peritoneal dialysis treatment, e.g. proteins. Since a number of trace elements are protein bound it is likely that those will be lost to an even higher amount than in different modalities of hemodialysis. Peritoneal dialysis may as well be facilitated by the use of a machine that drain and fill the peritoneal cavity automatically during night time (automated peritoneal dialysis).

The composition of the invention, thus the dialysis formulation, is a formulation for dialysis treatment. Such formulations are used in all the above dialysis techniques contain mainly electrolytes like sodium, magnesium, calcium, potassium, an acid/base buffer system and optionally glucose or a glucose-like compound. All the components in a dialysis formulation are selected to control the levels of electrolytes and the acid-base equilibrium within the blood and to remove waste materials from the blood.

Also, the dialysis formulation may be a citrate containing dialysis formulation of the invention is a formulation for dialysis treatment. Such formulations used in all the above dialysis techniques contain mainly electrolytes like sodium, magnesium, calcium, potassium, an acid/base buffer system and optionally glucose or a glucose-like compound. All the components in the formulation for dialysis treatment are selected to control the levels of electrolytes and the acid-base equilibrium within the blood and to remove waste materials from the blood.

Dialysis formulations, compositions for dialysis treatment, are today often prepared from different types of concentrates. These may be liquid concentrates of different degree of concentration, where the acid/-electrolyte part is separated from the buffer part. It may be provided as liquid concentrates divided between different compartments within a multi-compartment bag. These liquid concentrates are then mixed to prepare the ready to use dialysis fluid. This mixing may be performed by breaking a seal between the different compartments, but it may also be performed by having the different liquid concentrates being led from the different compartments to a fluid preparation unit for mixing therein into a dialysis fluid.

The treatment fluids may be prepared from concentrated volumes of 0.5-8 L in bags for bedside use, or prepared from concentrated volumes of 5-20 L in canisters, which still are for bedside use. The treatment fluids may also be prepared from concentrates in central tanks in volumes of 300-1000 L.

The concentrates may also be provided as dry concentrates for dilution into liquid concentrates and further mixing within a fluid preparation unit into a dialysis fluid.

As mentioned above, the dialysis fluid contains an acid for the acid/base buffer system. Most commonly, the acid used within dialysis fluids has been acetic acid. Lactic acid is another suitable acid to be included in the dialysis fluid.

Heparin is used as an agent for anticoagulation during dialysis for example as an anticoagulation agent in the hemodialysis methods described above, but due to its drawbacks citrate has been introduced and developed as an alternative anticoagulation agent in hemodialysis.

As described above, the dialysis fluid is provided as a two-, or multi-part solution before its use as dialysis fluid. The two-part solution comprises an acid solution and a base solution. However, the acid solution of these two-part solutions comprises components which may form complex and precipate in the concentrate solution. The both solutions are mixed to form a neutral and for patient compliant solution.

However, there are no dialysis formulations available today which comprise selenium.

The dialysis formulations shall be substantially physiologically acceptable regarding concentration of electrolytes and pH.

Most commonly the treatment fluids, such as dialysis fluids and replacement fluids, are provided from concentrates, for example as fluids, kept separate from each other until the time point for treatment. Then, they are prepared as ready to use treatment fluids.

The concentrates may be in different forms, the bicarbonate buffer concentrate is usually in form of dry powder, while the concentrates of electrolytes are in form of fluid. Depending on the concentrate of electrolytes selected, sodium chloride may be provided in powder form. The concentrates in form of powder are dissolved with a diluent before mixing with the other parts. The diluent is preferably sterile water or water free from electrolytes.

The concentrates are usually intended for dilution according to 1:35, 1:45 or 1:200.

There are concentrates commercially available on the market. Examples of products suitable for treatment fluids are Softpac™, SelectBag™ One, and Hemosol are products suitable for treatment fluids. Also citrate containing formulations in form of concentrates are available, for example, SelectBag™ Citrate and Prismocitrate™. These may form the basis for the dialysis fluid herein described.

In one embodiment of the invention, the dialysis formulation for dialysis treatment may be provided as a concentrate.

Another embodiment of the invention, the dialysis formulation for dialysis treatment may be provided as a ready to use fluid, thus as a ready to use treatment fluid, such as dialysis fluid or replacement fluid.

In one embodiment of the invention is a dialysis formulation comprising trace element selenium (Se) which is essentially free of chromium (Cr), manganese (Mn), and copper (Cu). The different dialysis formulations comprising selenium (Se) as herein described is essentially free of one or more of the trace elements selected from chromium (Cr), manganese (Mn), and copper (Cu). For example, the dialysis formulation is essentially free from chromium (Cr); or the dialysis formulation is essentially free from manganese (Mn); or the dialysis formulation is essentially free from copper (Cu). Another dialysis formulation is essentially free from chromium (Cr) and manganese (Mn).

The dialysis formulation may also be essentially free of aluminum (Al), and arsenic (As). These trace elements have disadvantageous effects and shall be avoided in the fluids as far as possible.

In one embodiment of the invention a dialysis formulation comprising the trace element selenium (Se); with the proviso that the dialysis formulation does not consist of sodium selenite pentahydrate, sodium chloride, hydrochloric acid and water.

Another embodiment of the invention is a composition comprising trace element selenium (Se); with the proviso that the said composition is essentially free of chromium (Cr), manganese (Mn), copper (Cu), and with the proviso that the composition does not consist of sodium selenite pentahydrate, sodium chloride, hydrochloric acid and water, is also provided by the invention.

The dialysis formulation may also comprise phosphate. Phosphate may be present in a concentration of 0-1.3 mM, preferably in a concentration of 0.6-1.2 mM, more preferably in a concentration of 0.8-1.0 mM.

A dialysis formulation (Formulation A) intended for intermittent dialysis treatment, the ready to use composition may comprise the following components:

| | |
|---|---|
| Sodium Na$^+$ | 130-150 mM |
| Potassium K$^+$ | 0-4 mM |
| Magnesium Mg$^{2+}$ | 0-0.75 mM |
| Calcium Ca$^{2+}$ | 1-1.75 mM |
| Acid (e.g. acetate, lactate) | 3-4 mEq/L |
| Glucose | 0-2 g/l |
| Bicarbonate (HCO$_3^-$) | 20-40 mM |
| Phosphate | 0-1.3 mM |
| Selenium Se | 0.6-1.8 μM |
| Rubidium Rb | 0-2.7 μM |
| Cobalt Co | 0-0.02 μM |
| Molybdenum Mo | 0-0.02 μM |
| Zinc Zn | 0-11 μM |

A dialysis formulation (Formulation B) is intended for peritoneal dialysis treatment, the ready to use formulation may comprise the following components:

| | |
|---|---|
| Glucose | 0-4.5% |
| Glucose polymer | 0-8% |
| Sodium Na$^+$ | 110-132 mM |
| Magnesium Mg$^{2+}$ | 0.25-0.4 mM |
| Calcium Ca$^{2+}$ | 1-2 mM |
| Acid (e.g. acetate, lactate) | 30-40 mEq/L |
| Bicarbonate (HCO$_3^-$) | 30-40 mM |
| Amino acids | 1-1.5% |
| Phosphate | 0-1.3 mM |
| Selenium Se | 0.6-1.8 μM |
| Rubidium Rb | 0-2.7 μM |
| Cobalt Co | 0-0.02 μM |
| Molybdenum Mo | 0-0.02 μM |
| Zinc Zn | 0-11 μM |

A dialysis formulation (Formulation C) suitable as treatment fluid is provided and presented below. The treatment fluid may be used both as dialysis fluid and as replacement fluid. When used as replacement fluid, it may be given as predilution, post-dilution, or a combination thereof.

| | |
|---|---|
| Calcium Ca$^{2+}$ | 1.75 mM |
| Magnesium Mg$^{2+}$ | 0.5 mM |
| Sodium Na$^+$ | 140 mM |
| Potassium K$^+$ | 0-4 mM |
| Lactate | 3.0 mM |
| HCO$_3^-$ | 32 mM |
| Glucose | 4-7 mM |
| Phosphate | 0.6-1.3 mM |
| Selenium Se | 0.6-1.8 μM |
| Rubidium Rb | 0-2.7 μM |
| Cobalt Co | 0-0.02 μM |
| Molybdenum Mo | 0-0.02 μM |
| Zinc Zn | 0-11 μM |

The Formulations A, B, and C may also comprise chloride a, for example in an amount of 90-115 mM, such as 109.5-113.5 mM, to obtain electroneutrality.

Another embodiment is a dialysis formulation (Formulation D) comprising the following:

| | |
|---|---|
| Calcium Ca$^{2+}$ | 1.75 mM |
| Magnesium Mg$^{2+}$ | 0.5 mM |
| Sodium Na$^+$ | 140 mM |
| Potassium K$^+$ | 0-4 mM |
| Lactate | 3.0 mM |
| Bicarbonate HCO$_3^-$ | 32 mM |
| Glucose | 4-7 mM |
| Phosphate | 0-1.3 mM |
| Selenium Se | 0.6-1.8 μM |
| Rubidium Rb | 0-2.7 μM |
| Cobalt Co | 0-0.02 μM |
| Molybdenum Mo | 0-0.02 μM |
| Zinc Zn | 0-11 μM |

The dialysis formulation may also comprise chloride Cl$^-$, for example in an amount of 90-115 mM, such as 109.5-113.5 mM, to obtain electroneutrality. Formulation D may be combined with Formulation C, as dialysis fluid or as replacement fluid, and where one of the dialysis formulations contains an amount of phosphate, for example 0.6-1.3 mM. Further, the dialysis formulation may comprise 1.4-2.7 µM rubidium.

A further embodiment is a dialysis formulation (Formulation E) (replacement fluid) comprising the following

| | |
|---|---|
| Sodium Na$^+$ | 140 mM |
| Calcium Ca$^{2+}$ | 1.25 mM |
| Magnesium Mg$^{2+}$ | 0.6 mM |
| Potassium K$^+$ | 4.0 mM |
| Bicarbonate HCO$_3^-$ | 30 mM |
| Phosphate | 1.2 mM |
| Selenium Se | 0.6-1.8 µM |
| Rubidium Rb | 0-2.7 µM |
| Cobalt Co | 0-0.02 µM |
| Molybdenum Mo | 0-0.02 µM |
| Zinc Zn | 0-11 µM |

The dialysis formulation may also comprise chloride Cl$^-$, for example in an amount of 90-115 mM, such as 109.5-113.5 mM, to obtain electroneutrality Any of the two fluids, Formulation D and Formulation E, may be used as either replacement fluid or as dialysis fluid in a dialysis treatment.

Formulation D may be used in combination with Formulation E in dialysis treatment as dialysis fluid and replacement fluid, respectively.

Formulation F represents a dialysis formulation intended for intermittent dialysis treatment, the ready to use formulation may comprise the following components. Formulation F:

| | |
|---|---|
| Sodium Na$^+$ | 130-150 mM |
| Potassium K$^+$ | 0-4 mM |
| Magnesium Mg$^{2+}$ | 0-0.75 mM |
| Calcium Ca$^{2+}$ | 1-1.75 mM |
| Acid (e.g. acetate, lactate) | 3-4 mEq/L |
| Glucose | 0-2 g/l |
| Bicarbonate (HCO$_3^-$) | 20-40 mM |
| Phosphate | 0-1.3 mM |
| Selenium Se | 0.5-2.5 µM |
| Rubidium Rb | 1.1-4.7 µM |
| Copper Cu | 6.2-15.7 µM |
| Cobalt Co | 0-0.02 µM |
| Molybdenum Mo | 0-0.02 µM |
| Zinc Zn | 0-15.5 µM |

At least one of the dialysis formulations contains the trace elements when combined to the dialysis treatment.

The dialysis formulations may also be provided as dry powder concentrates. Dry concentrates, also called dialysis acid precursor, intended for hemodialysis treatment may be a powder comprising an acid, at least one magnesium salt, at least one calcium salt, glucose, and optionally potassium salt. Preferably the magnesium salt and the glucose are present as anhydrous components. The dialysis precursor formulation is then preferably stored in a moisture-resistant container having a vapor transmission rate less than 0.3 g/m2/d at 38 C/90% RH.

The magnesium salt may be selected from the group comprising anhydrous magnesium chloride, magnesium gluconate, magnesium citrate, magnesium lactate, magnesium α-ketoglutarate, and magnesium chloride 4.5-hydrate.

The calcium salt may be selected from the group comprising calcium chloride dihydrate, calcium chloride monohydrate, anhydrous calcium chloride, calcium gluconate, calcium citrate, calcium lactate, and calcium α-ketoglutarate. The acid may be selected from any physiologically acceptable acid available in dry powder form. The acid may be selected from, but not limited to, lactic acid, gluconic acid, glucono-δ-lactone, N-acetyl cysteine and α-lipoic acid.

The dialysis acid precursor may then be combined with a bicarbonate containing concentrate, and optionally with a sodium chloride containing concentrate. Dialysis acid precursors are further described in WO 2011161055 and WO 2011161056.

A dry powder concentrate is described (Formulation G) below:

| | | Conc in DACS (mM) | Conc in RFUDS (mM) |
|---|---|---|---|
| Sodium chloride | | 3500 | 100 |
| Potassium chloride | | 0-140 | 0-4 |
| Magnesium gluconate | | 17.5-35 | 0.5-1 |
| Calcium chloride dihydrate | | 35-61.25 | 1-1.75 |
| Acid * | | 105 | 3 |
| Glucose anhydrous | | 194.4 | 5.55 |
| Selenium Se | 0.6-1.8 µM | | |
| Rubidium Rb | 0-2.7 µM | | |
| Cobalt Co | 0-0.02 µM | | |
| Molybdenum Mo | 0-0.02 µM | | |
| Zinc Zn | 0-11 µM | | |

* the amount of acid is denoted in mEq/L.
The amounts of trace elements are the concentration in RFUDS.

In another embodiment the dry powder concentrate comprises the following (Formulation H):

| | | Conc in DACS (mM) | Conc in RFUDS (mM) |
|---|---|---|---|
| Sodium chloride | | 3500 | 100 |
| Potassium chloride | | 0-140 | 0-4 |
| Magnesium lactate | | 17.5-35 | 0.5-1 |
| Calcium gluconate | | 35-61.5 | 1-1.75 |
| Acid * | | 105 | 3 |
| Glucose anhydrous | | 194.4 | 5.55 |
| Selenium Se | 0.6-1.8 µM | | |
| Rubidium Rb | 0-2.7 µM | | |
| Cobalt Co | 0-0.02 µM | | |
| Molybdenum Mo | 0-0.02 µM | | |
| Zinc Zn | 0-11 µM | | |

* the amount of acid is denoted in mEq/L.
The amounts of trace elements are the concentration in RFUDS.

This concentrate comprises selenium in an amount to provide a ready to use fluid having a concentration of selenium of 0.6-1.8 µM.

Formulation G and Formulation H are intended for dilution 1:35 or 1:45.

A concentrate which may constitute the basis for the dry powder concentrate comprising trace elements like selenium and rubidium is further described in WO2011161055.

Formulation I is a concentrate comprising selenium/rubidium and intended for dilution 1:200 into a ready to use fluid:

| | Conc in DACS (mM) | Conc in RFUDS (mM) |
|---|---|---|
| Potassium chloride | 0-800 | 0-4 |
| Magnesium gluconate | 100-200 | 0.5-1 |
| Calcium chloride Dehydrate | 200-350 | 1-1.75 |
| Acid * | 600 | 3 |

-continued

|  | Conc in DACS (mM) | Conc in RFUDS (mM) |
| --- | --- | --- |
| Glucose anhydrous |  | 1110 | 5.55 |
| Selenium Se | 0.6-1.8 µM |  |  |
| Rubidium Rb | 0-2.7 µM |  |  |
| Cobalt Co | 0-0.02 µM |  |  |
| Molybdenum Mo | 0-0.02 µM |  |  |
| Zinc Zn | 0-11 µM |  |  |

\* the amount of acid is denoted in mEq/L.
The amounts of trace elements are the concentration in RFUDS.

Formulation J is also a dialysis formulation intended for dilution 1:200 before use.

|  |  | Conc in DACS (mM) | Conc in RFUDS (mM) |
| --- | --- | --- | --- |
| Potassium chloride |  | 0-800 | 0-4 |
| Magnesium lactate |  | 100-200 | 0.5-1 |
| Calcium gluconate |  | 200-350 | 1-1.75 |
| Acid * |  | 600 | 3 |
| Glucose anhydrous |  | 1110 | 5.55 |
| Selenium Se | 0.6-1.8 µM |  |  |
| Rubidium Rb | 0-2.7 µM |  |  |
| Cobalt Co | 0-0.02 µM |  |  |
| Molybdenum Mo | 0-0.02 µM |  |  |
| Zinc Zn | 0-11 µM |  |  |

\* the amount of acid is denoted in mEq/L.
The amounts of trace elements are the concentration in RFUDS.

Formulation I and Formulation J are to be combined with a sodium containing concentrate and a bicarbonate containing concentrate into a ready to use dialysis fluid, both are preferably provided as dry powder concentrate. Dry powder concentrates like Formulation I is further described in WO2011161056.

The dialysis formulations included herein below are the citrate containing dialysis formulations.

In one embodiment of the invention a citrate containing dialysis formulation comprises 0.1-1160 mM citrate and 0.6-1.8 µM selenium; preferably 0.1-40 mM citrate and 0.6-1.8 µM selenium. The citrate containing dialysis fluids are anticoagulation fluids as well as treatment fluids.

In one embodiment of the invention a citrate containing dialysis formulation (Formulation 1) comprises the following components when it is intended for continuous dialysis treatment, as anticoagulation fluid or treatment fluid, thus treatment of patients having acute kidney disorders:

| Sodium, Na$^+$ | 120-150 mM |
| --- | --- |
| Magnesium, Mg$^{2+}$ | 0-1.1 mM |
| Lactate | 0-4 mM |
| Bicarbonate | 0-40 mM |
| Citrate | 0.1-1160 mM |
| Potassium K$^+$ | 0-4 mM |
| Glucose | 0-7 mM |
| Calcium, Ca$^{2+}$ | 0-3 mM |
| Phosphate | 0-1.3 mM |
| Selenium, Se | 0.6-1.8 µM |
| Rubidium, Rb | 0-4.2 µM |
| Cobalt, Co | 0-0.02 µM |
| Molybdenum, Mo | 0-0.02 µM |
| Zinc, Zn | 0-11 µM |

More specifically the citrate containing dialysis formulation (Formulation 2) ready to use may have the following composition:

| Sodium, Na+ | 136-146 mM |
| --- | --- |
| Potassium, K+ | 0-5.0 mM |
| Magnesium, Mg2+ | 0.7-1.1 mM |
| Calcium, Ca2+ | 2.2-2.6 mM |
| Bicarbonate, HCO3− | 15-35 mM |
| Citrate | 0.1-40 mM |
| Glucose | 0-6 mM |
| Phosphate | 0-1.3 mM |
| Selenium, Se | 0.6-1.8 µM |
| Optionally, the dialysis formulation may also comprise | |
| Rubidium, Rb | 0-4.2 µM |
| Cobalt, Co | 0-0.02 µM |
| Molybdenum, Mo | 0-0.02 µM |
| Zinc, Zn | 0-11 µM |

In one embodiment of the invention a citrate containing dialysis formulation (Formulation 3) comprises the following components when it is intended for continuous dialysis treatment, as anticoagulation fluid or treatment fluid, thus treatment of patients having acute kidney disorders.

| Sodium, Na$^+$ | 120-150 mM |
| --- | --- |
| Magnesium, Mg$^{2+}$ | 0-1.1 mM |
| Lactate | 0-4 mM |
| Bicarbonate | 0-40 mM |
| Citrate | 0.1-1160 mM |
| Potassium K$^+$ | 0-4 mM |
| Glucose | 0-7 mM |
| Calcium, Ca$^{2+}$ | 0-3 mM |
| Phosphate | 0-1.3 mM |
| Selenium, Se | 0.5-1.8 µM |
| Rubidium, Rb | 0-4.7 µM |
| Cobalt, Co | 0-0.02 µM |
| Molybdenum, Mo | 0-0.02 µM |
| Zinc, Zn | 0-12.3 µM |
| Copper, Cu | 0-15.7 µM. |

In one embodiment of the invention a citrate containing dialysis formulation (Formulation 4) comprises the following components when it is intended to for continuous dialysis treatment, thus treatment of patients having acute kidney disorders:

| Sodium, Na$^+$ | 120-150 mM |
| --- | --- |
| Magnesium, Mg$^{2+}$ | 0-0.75 mM |
| Lactate | 0-4 mM |
| Bicarbonate | 0-40 mM |
| Citrate | 0-1160 mM |
| Potassium K$^+$ | 0-4 mM |
| Glucose | 0-7 mM |
| Calcium, Ca$^{2+}$ | 0-3 mM |
| Phosphate | 0-1.3 mM |
| Selenium, Se | 0.6-1.8 µM |
| Optionally, the dialysis formulation may also comprise | |
| Rubidium Rb | 0-4.2 µM |
| Cobalt Co | 0-0.02 µM |
| Molybdenum Mo | 0-0.02 µM |
| Zinc Zn | 0-11 µM |

When the citrate containing dialysis formulation (Formulation 5) is intended for intermittent dialysis treatment, the ready to use formulation may comprise the following components:

| Sodium, Na$^+$ | 130-150 mM |
| --- | --- |
| Potassium, K$^+$ | 0-4 mM |
| Magnesium, Mg$^{2+}$ | 0-0.75 mM |
| Calcium, Ca$^{2+}$ | 0.5-2.25 mM |

-continued

| | |
|---|---|
| Citrate | 0.25-6 mM |
| Glucose | 0-2 g/l |
| Bicarbonate, $HCO_3^-$ | 20-40 mM |
| Phosphate | 0-1.3 mM |
| Selenium, Se | 0.6-1.8 µM |
| Optionally, the dialysis formulation may also comprise | |
| Rubidium, Rb | 0-4.2 µM |
| Cobalt, Co | 0-0.02 µM |
| Molybdenum, Mo | 0-0.02 µM |
| Zinc, Zn | 0-0.76 µM |

An example of Formulation 5 contains, 0.67-1 mM citrate. Calcium may be present in a concentration of 1-1.75 mM.

When the citrate containing dialysis formulation (Formulation 6) is intended for peritoneal dialysis treatment, the ready to use dialysis formulation may comprise the following components:

| | |
|---|---|
| Glucose | 0-5% |
| Glucose polymer | 0-10% |
| Sodium, $Na^+$ | 100-132 mM |
| Magnesium, $Mg^{2+}$ | 0.25-0.75 mM |
| Calcium, $Ca^{2+}$ | 1-3 mM |
| Lactate | 0-40 mM |
| Bicarbonate ($HCO_3^-$) | 0-40 mM |
| Amino acids | 0-2% |
| Citrate | 0.01-10 mM |
| Phosphate | 0-1.3 mM |
| Selenium, Se | 0.6-1.8 µM |
| Optionally, the dialysis formulation may also comprise | |
| Rubidium Rb | 0-4.2 µM |
| Cobalt Co | 0-0.02 µM |
| Molybdenum Mo | 0-0.02 µM |
| Zinc Zn | 0-11 µM |

In one embodiment of the present invention the citrate containing formulation is an anticoagulation fluid comprising selenium.

This anticoagulation fluid may comprise 8-50 mM citrate, for example 10-40 mM citrate and selenium. The anticoagulation fluid is a ready to use dialysis formulation.

In another embodiment of the invention a multipart fluid system is provided. This multipart fluid system comprises an anticoagulation fluid and at least one treatment fluid wherein the anticoagulation fluid comprises at least 8 mM citrate and 0-122 µM selenium, and the at least one treatment fluid comprises 0.5-8 mM citrate and 0-3 µM selenium, for example 0-1.8 µM selenium, with the proviso that at least one of anticoagulation fluid and treatment fluid contains selenium. A multipart fluid system, and system thereof, is described in WO 2010112538.

A multipart fluid system (Formulation 7) may comprise an anticoagulation fluid, dialysis fluid, and replacement fluid (post) as described below.

| Anticoagulation fluid: | |
|---|---|
| Citrate/citric acid | 10-1160 mM |
| Sodium Na+ | 135-140 mM |
| Potassium K+ | 0.4 mM |
| Glucose | 0-7 mM |
| Phosphate | 0-1.2 mM |
| Selenium Se | 2.5-122 µM |
| Rubidium Rb | 0-215 µM |

-continued

| Anticoagulation fluid: | |
|---|---|
| Cobalt Co | 0-1.36 µM |
| Molybdenum Mo | 0-1.67 µM |
| Zinc Zn | 0-61.2 µM |

The anticoagulation fluid is combined with treatment fluid(s), such as dialysis fluid and post-replacement fluid with the following compositions. Rubidium may be present in an amount of, for example 4.68-215 µM. The dialysis formulation may comprise zinc in an amount of 0.50-61.2 µM.

| Dialysis fluid: | |
|---|---|
| Magnesium, $Mg^{2+}$ | 0-0.9 mM |
| Sodium, $Na^+$ | 120-150 mM |
| Lactate | 0-4 mM |
| Bicarbonate | 0-30 mM |
| Citrate | 0-6 mM |
| Potassium $K^+$ | 0-4 mM |
| Glucose | 0-7 mM |
| Calcium, $Ca^{2+}$ | 0-3 mM |
| Phosphate | 0-1.3 mM |
| Selenium, Se | 0.6-1.8 µM |
| Optionally, the dialysis formulation may also comprise | |
| Rubidium Rb | 0-4.2 µM |
| Cobalt Co | 0-0.02 µM |
| Molybdenum Mo | 0-0.02 µM |
| Zinc Zn | 0-11 µM |

| Post-replacement fluid: | |
|---|---|
| Magnesium, $Mg^{2+}$ | 0-0.9 mM |
| Sodium, $Na^+$ | 120-150 mM |
| Lactate | 0-4 mM |
| Bicarbonate | 0-32 mM |
| Citrate | 0-6 mM |
| Potassium $K^+$ | 0-4 mM |
| Glucose | 0-7 mM |
| Calcium, $Ca^{2+}$ | 0-3 mM |
| Phosphate | 0-1.3 mM |
| Selenium, Se | 0.6-1.8 µM |
| Optionally, the dialysis formulation may also comprise | |
| Rubidium Rb | 0-4.2 µM |
| Cobalt Co | 0-0.02 µM |
| Molybdenum Mo | 0-0.02 µM |
| Zinc Zn | 0-11 µM |

Another embodiment of the invention is a multipart system (Formulation 8) comprising the following anticoagulation fluid, dialysis fluid and post-replacement fluid.

| Anticoagulation fluid | |
|---|---|
| Citrate | 12 mM |
| Sodium Na | 136 mM |
| Phosphate | 0-1.3 mM |
| Selenium, Se | 0.6-1.8 µM |
| Optionally, the dialysis formulation may also comprise | |
| Rubidium Rb | 0-4.2 µM |
| Cobalt Co | 0-0.02 µM |
| Molybdenum Mo | 0-0.02 µM |
| Zinc Zn | 0-0.76 µM |

The anticoagulation fluid may also comprise chloride $Cl^-$ or in an amount of about 106 mM.

| Dialysis fluid | |
| --- | --- |
| Magnesium Mg$^{2+}$ | 0.5 mM |
| Sodium Na$^+$ | 140 mM |
| Chloride Cl$^-$ | 106 mM |
| Lactate | 3 mM |
| Bicarbonate HCO$_3^-$ | 32 mM |
| Phosphate | 0-1.3 mM |
| Selenium, Se | 0.6-1.8 µM |
| Optionally, the dialysis formulation may also comprise | |
| Rubidium Rb | 0-4.2 µM |
| Cobalt | 0-0.02 µM |
| Molybdenum | 0-0.02 µM |
| Zinc | 0-11 µM |

| Replacement fluid | |
| --- | --- |
| Calcium Ca$^{2+}$ | 1.25 mM |
| Magnesium Mg$^{2+}$ | 0.6 mM |
| Sodium Na$^+$ | 140 mM |
| Potassium K$^+$ | 4.0 mM |
| Chloride Cl$^-$ | 115.9 mM |
| Bicarbonate HCO$_3^-$ | 30 mM |
| Phosphate HPO$_4^{2-}$ | 1.2 mM |
| Selenium, Se | 0.6-1.8 µM |
| Optionally, the dialysis formulation may also comprise | |
| Rubidium Rb | 0-4.2 µM |
| Cobalt Co | 0-0.02 µM |
| Molybdenum Mo | 0-0.02 µM |
| Zinc Zn | 0-11 µM |

A further embodiment of the invention is a multipart system (Formulation 9) comprising the following anticoagulation fluid, dialysis fluid and post-replacement fluid.

| Anticoagulation fluid | |
| --- | --- |
| Citrate | 18 mM |
| Sodium Na$^+$ | 140 mM |
| Chloride Cl$^-$ | 86 mM |
| Phosphate | 0-1.3 mM |
| Selenium, Se | 0.6-1.8 µM |
| Optionally, the dialysis formulation may also comprise | |
| Rubidium Rb | 0-4.2 µM |
| Cobalt Co | 0-0.02 µM |
| Molybdenum Mo | 0-0.02 µM |
| Zinc Zn | 0-11 µM |

| Dialysis fluid | |
| --- | --- |
| Magnesium Mg$^{2+}$ | 0.75 |
| Sodium Na$^+$ | 140 mM |
| Potassium K$^+$ | 4 mM |
| Chloride Cl$^-$ | 120.5 mM |
| Lactate | 0-3 mM |
| Bicarbonate HCO$_3^-$ | 22 mM |
| Glucose | 6.1 mM |
| Phosphate | 0-1.3 mM |
| Selenium, Se | 0.6-1.8 µM |
| Optionally, the dialysis formulation may also comprise | |
| Rubidium Rb | 0-4.2 µM |
| Cobalt Co | 0-0.02 µM |
| Molybdenum Mo | 0-0.02 µM |
| Zinc Zn | 0-11 µM |

| Replacement fluid | |
| --- | --- |
| Calcium Ca$^{2+}$ | 1.25 mM |
| Magnesium Mg$^{2+}$ | 0.6 mM |
| Sodium Na$^+$ | 140 mM |
| Potassium K$^+$ | 4.0 mM |
| Chloride Cl$^-$ | 115.9 mM |
| Bicarbonate HCO$_3^-$ | 30 mM |
| Phosphate | 1.2 mM |
| Selenium, Se | 0.6-1.8 µM |
| Optionally, the dialysis formulation may also comprise | |
| Rubidium Rb | 0-4.2 µM |
| Cobalt Co | 0-0.02 µM |
| Molybdenum Mo | 0-0.02 µM |
| Zinc Zn | 0-11 µM |

In one embodiment the invention the citrate containing formulation (Formulation 10) is part of a multipart fluid system comprising the following fluids:

| Anticoagulation fluid: | |
| --- | --- |
| Calcium Ca$^{2+}$ | 2.0-2.4 mM (2.25) |
| Magnesium Mg$^{2+}$ | 0.8-1.0 mM (0.9) |
| Sodium Na$^+$ | 130-150 mM (140) |
| Potassium K$^+$ | 0-4 mM (3) |
| Chloride Cl$^-$ | 40-80 mM (59) |
| Phosphate (total) | 0-1.2 mM (0.8) |
| Citrate (total) | 18-40 mM (30) |
| Selenium, Se | 0.6-1.8 µM |
| Optionally, the dialysis formulation may also comprise | |
| Rubidium Rb | 0-2.7 µM |
| Cobalt Co | 0-0.02 µM |
| Molybdenum Mo | 0-0.02 µM |
| Zinc Zn | 0-11 µM |

Treatment fluid (being the same or different as dialysis fluid and replacement fluid):

| Treatment fluid: | |
| --- | --- |
| Sodium Na$^+$ | 130-150 mM, (such as 140 mM) |
| Calcium Ca$^{2+}$ | 2.0-2.4 mM (such as 2.1) |
| Magnesium Mg$^{2+}$ | 0.8-1.0 mM (such as 0.85) |
| Potassium K$^+$ | 0-4 mM (such as 3) |
| Chloride Cl$^-$ | 100-140 mM (such as 120) |
| Phosphate (total) | 0-1.2 mM (such as 0.8) |
| Citrate (total) | 3-7 mM (such as 5) |
| HCO$_3^-$ (total) | 16 mM |
| Selenium, Se | 0.6-1.8 µM |
| Optionally, the dialysis formulation may also comprise | |
| Rubidium Rb | 0-4.2 µM |
| Cobalt Co | 0-0.02 µM |
| Molybdenum Mo | 0-0.02 µM |
| Zinc Zn | 0-11 µM |

A specific example of Formulation 10 is presented below as Formulation 11. This multipart system comprises an anti-coagulation fluid (Formulation 11A) and a treatment fluid (Formulation 11B) suitable as well as dialysis fluid and replacement fluid:

| Anticoagulation fluid (Formulation 11A): | |
| --- | --- |
| Sodium Na$^+$ | 140 mM |
| Calcium Ca$^{2+}$ | 2.25 mM |
| Magnesium Mg$^{2+}$ | 0.9 mM |
| Potassium K$^+$ | 3 mM |
| Chloride Cl$^-$ | 59 mM |

-continued

Anticoagulation fluid (Formulation 11A):

| | |
|---|---|
| Phosphate (total) | 0.8 mM |
| Citrate (total) | 30 mM |
| Selenium, Se | 0.6-1.8 µM |
| Optionally, the dialysis formulation may also comprise | |
| Rubidium Rb | 0-4.2 µM |
| Cobalt Co | 0-0.02 µM |
| Molybdenum Mo | 0-0.02 µM |
| Zinc Zn | 0-11 µM |

Treatment fluid (Formulation 11B): (being the same or different as dialysis fluid and replacement fluid)

| | |
|---|---|
| Sodium Na$^+$ | 140 mM |
| Calcium Ca$^{2+}$ | 2.1 mM |
| Magnesium Mg$^{2+}$ | 0.85 mM |
| Potassium K$^+$ | 3 mM |
| Chloride Cl$^-$ | 120 mM |
| Phosphate (total) | 0.8 mM |
| Citrate (total) | 5 mM |
| HCO$_3^-$ (total) | 16 mM |
| Selenium, Se | 0.6-1.8 µM |
| Optionally, the composition may also comprise | |
| Rubidium Rb | 0-4.2 µM |
| Cobalt Co | 0-0.02 µM |
| Molybdenum Mo | 0-0.02 µM |
| Zinc Zn | 0-11 µM |

In one embodiment of the invention the citrate containing dialysis formulation comprising selenium is provided as dry powder concentrate.

The citrate containing dialysis formulation may also be provided as dry powder concentrate. Dry concentrates, also called dry powder concentrate or dialysis acid precursor, intended for hemodialysis treatment may be a powder comprising an acid, at least one magnesium salt, at least one calcium salt, glucose, and optionally potassium salt. Preferably the magnesium salt and the glucose are present as anhydrous components. The dialysis precursor composition is then preferably stored in a moisture-resistant container having a vapor transmission rate less than 0.3 g/m2/d at 38 C/90% RH. The acid may be selected from lactic acid, citric acid, gluconic acid, glucono-δ-lactone, N-acetyl cysteine and α-lipoic acid.

The magnesium salt may be selected from the group comprising anhydrous magnesium chloride, magnesium gluconate, magnesium citrate, magnesium lactate, magnesium α-ketoglutarate, and magnesium chloride 4.5-hydrate.

The calcium salt may be selected from the group comprising calcium chloride dihydrate, calcium chloride monohydrate, anhydrous calcium chloride, calcium gluconate, calcium citrate, calcium lactate, and calcium α-ketoglutarate.

The dialysis acid precursor may then be combined with a bicarbonate containing concentrate, and optionally with a sodium chloride containing concentrate. Dialysis acid precursors are further described in WO 2011161055 and WO 2011161056.

The dry powder concentrate is intended to be diluted into a ready to use solution. The concentration of the components are mentioned as 'Conc in DACS (mM)' which means the concentration in diluted A concentrate solution, and as RFUDS which means the concentrations in the ready for use dialysis solution.

In another embodiment (Formulation 12) the dry powder concentrate comprises the following

| | Conc in DACS (mM) | Conc in RFUDS (mM) |
|---|---|---|
| Sodium chloride | 3500 | 100 |
| Potassium chloride | 0-140 | 0-4 |
| Magnesium gluconate | 17.5-35 | 0.5-1 |
| Calcium chloride Dehydrate | 35-61.25 | 1-1.75 |
| Citric acid | 35 | 1 |
| Glucose anhydrous | 194.4 | 5.55 |
| Selenium Se | 0.6-1.8 µM | |
| Rubidium Rb | 0-8.4 µM | |
| Cobalt Co | 0-0.04 µM | |
| Molybdenum Mo | 0-0.02 µM | |
| Zinc Zn | 0-1.52 µM | |

The amounts of trace elements are the concentration in RFUDS.

An alternative embodiment is described in the following (Formulation 13):

| | Conc in DACS (mM) | Conc in RFUDS (mM) |
|---|---|---|
| Sodium chloride | 3500 | 100 |
| Potassium chloride | 0-140 | 0-4 |
| Magnesium lactate | 17.5-35 | 0.5-1 |
| Calcium gluconate | 35-61.25 | 1-1.75 |
| Citric acid | 35 | 1 |
| Glucose anhydrous | 194.4 | 5.55 |
| Selenium Se | 0.6-1.8 µM | |
| Rubidium Rb | 0-8.4 µM | |
| Cobalt Co | 0-0.04 µM | |
| Molybdenum Mo | 0-0.02 µM | |
| Zinc Zn | 0-22 µM | |

The amounts of trace elements are the concentration in RFUDS.

Formulation 12 and Formulation 13 are intended for dilution 1:35 or 1:45. These concentrates comprise selenium in an amount to provide a ready to use fluid having a concentration of selenium of 0.6-1.8 µM.

A concentrate which may constitute the basis for the dry powder concentrate comprising trace elements like selenium and rubidium is further described in WO 2011161055.

Another embodiment of the invention is a citrate containing dialysis formulation (Formulation 14) in form of dry powder concentrate comprising selenium. Formulation 14 is intended for dilution 1:200 into a ready to use fluid:

| | Conc in DACS (mM) | Conc in RFUDS (mM) |
|---|---|---|
| Potassium chloride | 0-800 | 0-4 |
| Magnesium gluconate | 100-200 | 0.5-1 |
| Calcium chloride Dehydrate | 200-350 | 1-1.75 |
| Citric acid | 200 | 1 |
| Glucose anhydrous | 1110 | 5.55 |
| Selenium Se | 0.6-1.8 µM | |
| Rubidium Rb | 0-8.4 µM | |
| Cobalt Co | 0-0.04 µM | |
| Molybdenum Mo | 0-0.02 µM | |
| Zinc Zn | 0-22 µM | |

The amounts of trace elements are the concentration in RFUDS.

An alternative formulation is presented below (Formulation 15). Also this formulation is a citrate containing formulation comprising selenium and intended for dilution 1:200.

|  | Conc in DACS (mM) | Conc in RFUDS (mM) |
| --- | --- | --- |
| Potassium chloride |  | 0-800 | 0-4 |
| Magnesium lactate | 100-200 | 0.5-1 |
| Calcium gluconate | 200-350 | 1-1.75 |
| Citric acid | 200 | 1 |
| Glucose anhydrous | 1110 | 5.55 |
| Selenium Se | 0.6-1.8 µM |  |
| Rubidium Rb | 0-8.4 µM |  |
| Cobalt Co | 0-0.04 µM |  |
| Molybdenum Mo | 0-0.02 µM |  |
| Zinc Zn | 0-22 µM |  |

The amounts of trace elements are the concentration in RFUDS.

Formulation 14 and Formulation 15 are to be combined with a sodium containing concentrate and a bicarbonate containing concentrate into a ready to use dialysis fluid, both may be provided as dry powder concentrate. A dry powder concentrate is further described in WO 2011161056.

Experimental Data

Trace element concentrations have been analyzed in effluent obtained from hemodialysis (HD) patients at the end of their dialysis session. Those concentrations (compiled in Table A) reflects the true loss of trace elements since parts of the trace elements are protein bound there will be a lower actual loss than what would be expected from the measured concentrations in plasma.

TABLE A

|  | Effluent concentration ± SD (µM) |
| --- | --- |
| Selenium | 0.01 ± 0.005 |
| Rubidium | 0.31 ± 0.17 |
| Molybdenum | 0.003 ± 0.002 |
| Cobalt | 0.0015 ± 0.002 |
| Zinc | 0.017 ± 0.01 |
| Copper | 0.026 ± 0.015 |
| Chromium | 0.0043 ± 0.008 |
| Manganese | 0.005 ± 0.005 |

Further, to investigate the trace element status of dialysis patients, the plasma, whole blood, and effluent content of the trace elements Cr, Cu, Mn, Co, Se, Mo, Rb, and Zn have been examined. Blood samples were taken at the initiation of dialysis as well as in conjunction to the end of the dialysis session. Effluent samples were taken close to the end of the dialysis session (Table A). This was compared to blood samples from a healthy control group. In addition we also investigated if there were any correlations between any trace elements AGE-formation, oxidative stress, and inflammation in hemodialysis patients, with and without diabetes.

Materials and Methods

Patients and Sampling

In the study participated 47 hemodialysis patients. These 47 hemodialysis patients (34 female and 13 male), were divided into 30 non-diabetic and 17 with diabetes mellitus, with an average age of 67 (Table 1). All patients received dialysis 3-5 h, 3-4 times per week. Whole blood and plasma samples for trace element analysis were obtained pre- and post-midweek dialysis treatment in 6 ml trace element-free EDTA tubes (BD Vaccutainer®, Stockholm, Sweden). In addition effluent samples were taken post-treatment in 50 ml trace element-free tubes. In addition, the same samples were taken at one occasion from a healthy control group. The control group included 51 persons (20 female and 31 male), with an average age of 22.

Trace Element Analysis

Analysis of all trace elements was performed by inductively coupled plasma-mass spectrometry (ICP-MS; Thermo X7, Thermo Elemental, Winsford, UK). For plasma and blood a sample volume of 250 µL was diluted 10 times with an alkaline solution according to Bárány et al. The effluent was analysed in acidic condition, i.e. concentrated nitric acid ($HNO_3$) was added to the samples to a final concentration of 2%. Using the dilute solution or 2% $HNO_3$ as a carrier/rinsing fluid, the samples were introduced in a segment-flow mode. The analytical accuracy was confirmed against reference material (SERONORM Trace Elements Blood/Serum; SERO AS, Billingstad, Norway) and for effluent solution Riverine Water Reference Material for Trace Metals, SLRS-2; National Research Council Canada, Ottawa Canada. The obtained values for the control samples showed good agreement with the recommended and certified concentrations [15].

AGE-Formation

Plasma pentosidine samples were taken pre- and post-dialysis treatment from 24 non-diabetic and 16 diabetic HD patients and compared with plasma pentosidine samples from 51 healthy controls. Samples were analysed by HPLC as previous described [13].

Acute Inflammation

Plasma samples were taken from 24 non-diabetic and 16 diabetic HD patients pre- and post-dialysis and compared with plasma samples from 51 healthy controls. The samples were analysed for PTX-3 using Human Pentraxin 3/TSG-14 Quantikine ELISA according to manufactures' instructions (R&D systems).

Oxidative Stress

Plasma samples were taken from 24 non-diabetic and 16 diabetic HD patients pre- and post-dialysis and compared with plasma samples from 51 control subjects. Analyses were performed by using "highly sensitive 8-OHdG check ELISA" according to manufactures' instructions (Fischer scientific).

Statistics

All data are shown as mean value±SEM. Markers for AGE, inflammation and oxidative stress are shown as mean values of two analyses of the same samples. The different groups i.e. all HD patients, HD non-diabetic, HD diabetic and healthy controls, were compared and evaluated by t-test or ANOVA and samples taken pre- and post-dialysis of each patient was analysed by ANOVA paired t-test.

Results

Trace Elements

The whole blood analysis of trace elements represents the total blood content of the metals and can be divided into two parts, intra- and extra-cellular. The extra-cellular compartment can be further divided into free- and complex-bound phases. The free part of the extracellular portion is freely exchangeable across the dialysis membrane, while the complex-bound part may be partially exchangeable.

Chromium was found both in blood and plasma, in higher concentration in HD patients compared to controls (3.3±0.3 µg/l plasma pre-dialysis and 0.3±0.02 µg/l plasma controls, P<0.001) (Table 1). The chromium concentrations were significantly increased during dialysis treatment both in plasma and blood by up to 60% (FIG. 2), in diabetic as well as non-diabetic patients (P<0.001) (FIG. 1A). The non-diabetic group had higher plasma chromium concentrations post-dialysis compared to the diabetic HD group (3.8±0.4 µg/l and 2.5±0.4 µg/l, P=0.004) (FIG. 1A).

Manganese concentrations were twice as high before dialysis in all HD patients compared with controls (17±1.3

μg/l and 9.2±0.4 μg/l, P<0.001), (Table 1). There was no difference between the two HD groups, although both HD groups showed a significant increase of manganese in blood samples during dialysis (17±1.3 μg/l increased to 19±1.4 μg/l for non-diabetic HD patients and 17±2.1 μg/l to 20±2.7 μg/l increased for diabetic HD, P<0.001 and P=0.037) (FIG. 1B).

Cobalt was found both in plasma and whole blood samples of all HD patients. Concentration of cobalt was increased in all HD patients compared to controls (0.6±0.03 μg/l in plasma pre-dialysis of HD patients and 0.4±0.02 μg/l in plasma from controls, P<0.001) (Table 1). There was a ~15% increase in plasma cobalt concentrations during dialysis in both the diabetic and the non-diabetic HD patients (FIGS. 1C and 2).

Copper was present in all samples and the highest concentrations were found in plasma. The concentrations in both plasma and whole blood increased slightly during dialysis by ~4% (FIG. 2). Compared with controls, diabetic HD patients had significantly higher copper concentrations in all blood samples (1059±45 μg/l plasma controls and 1173±56 μg/l from plasma diabetic HD patients, P=0.018). There were though no significant differences in copper concentrations between diabetic and non-diabetic HD patients (FIG. 1D, Table 1).

Zinc concentrations were ten times higher in the whole blood samples compared with plasma in all groups (Table 1). Zinc concentrations increased slightly during dialysis by ~5% both in plasma and whole blood (FIG. 2). There was a significant higher zinc concentration in all dialysis patients compared with controls (5610±138 μg/l in whole blood pre-dialysis and 5189±124 μg/l in whole blood controls, P=0.025) (Table 1); however, when comparing the two different HD groups separately, the higher zinc concentration was only significant in the whole blood samples from non-diabetic HD group compared with controls, P=0.032, (FIG. 1E).

Selenium concentrations were significantly lower in all HD patients compared with controls and the highest concentrations were found in whole blood. The values increased slightly during dialysis but did not reach normal levels of healthy controls, P<0.001 (Table 1, FIG. 2). The lowest concentrations of selenium were found in the diabetic HD group and there were a significant difference between the two HD groups, both comparing blood and plasma levels pre- and post-HD treatment (70±2.6 μg/l in blood samples pre-dialysis from non-diabetic HD patients and 59±4 μg/l in blood samples pre-dialysis from diabetic HD patients P=0.018; and 58±2 μg/l and 44±3 μg/l in plasma samples pre-dialysis in the different HD groups, P<0.001). The diabetic HD patients also showed a significant increase of selenium in whole blood during dialysis, P=0.0045 (FIG. 1F). There was also a significant correlation between selenium and 8-OHdG in the diabetic HD patients, as mentioned previously (FIG. 4).

Rubidium was predominantly found in whole blood samples and the concentration was reduced by half in all HD patients compared to control samples, P<0.001 (Table 1). The concentrations decreased further by ~20% in plasma during dialysis (FIG. 2). There were no differences in rubidium concentrations between the HD groups (FIG. 1G).

The concentrations of molybdenum in all HD patients were higher than those in control subjects with the highest concentrations in plasma (Table 1). The concentrations decreased during dialysis treatment both in plasma and whole blood by ~50% (FIG. 2), and almost reached control concentrations (Table 1) (FIG. 1H). The highest concentration of molybdenum was found in the diabetic group pre-dialysis and here the values were also significantly reduced by 50% during dialysis (3.1±0.4 μg/l and 1.2±0.2 μg/l in plasma, P<0.001) (FIG. 1H).

AGE Formation

High plasma pentosidine concentrations are linked with inflammation, oxidative stress and diabetic complications. Pentosidine, produced in the Malliard reaction, was chosen as a biomarker for formation of AGE [17]. Plasma pentosidine concentrations were up to ten times higher in dialysis patients compare with controls (Table 2). Non-diabetic HD patients had the highest concentration of pentosidine both pre- and post-dialysis. There was a significant difference between the HD groups post-dialysis, 1976±217 and 1510±239, P=0.046 (FIG. 3A).

Acute Inflammation

The acute phase protein PTX-3 is produced by the major cell types involved in atherosclerotic lesions in response to inflammatory stimuli and elevated plasma levels are found in several conditions including acute coronary syndromes. PTX-3 is a rapid and sensitive marker and has previously been shown to increase during HD treatment [4]. PTX-3 concentrations were significantly elevated in HD-patients pre-dialysis compared with controls (1.8±0.2 ng/ml and 0.7±0.02 ng/ml, P<0.001), and the levels were increased even further during dialysis. The post-dialysis values were 4 times higher than in the controls (Table 2). We found an increased, but not significant, PTX-3 concentration both pre- and post-dialysis in the diabetic-HD group compared to the non-diabetic HD group. Both HD groups had significant increased plasma concentrations post-dialysis compared to pre-treatment (FIG. 3B).

Oxidative Stress

Figure 4:
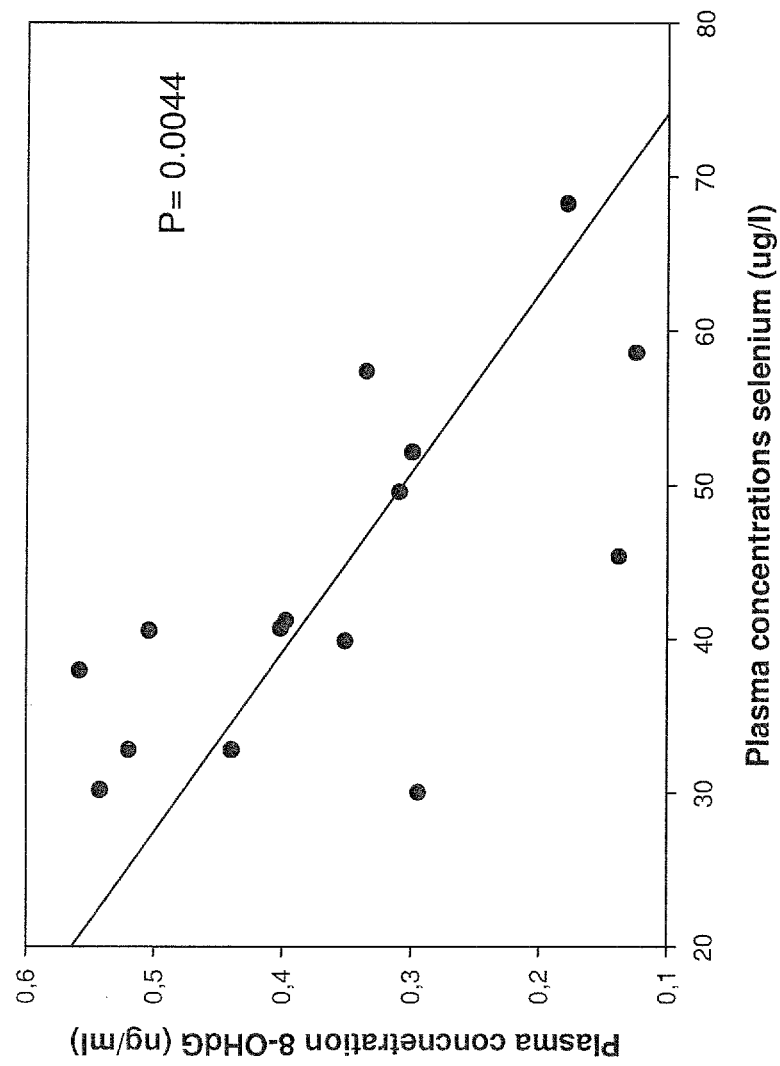
FIG. 4 shows the correlation between selenium and markers for oxidative stress (8-OHdG) in diabetic HD patients.

Oxidative stress was evaluated by measuring 8-OHdG, which is one of the predominant forms of free radical-induced lesions of DNA upon oxidation. 8-OHdG concentration is known to be increased in diabetic patients and can serve as a biomarker for oxidative DNA damage related to hyperglycemia and micro-vascular damage [5]. In our study, 8-OHdG levels in all HD patients were elevated pre-dialysis compared with those from the control group (0.34±0.02 ng/ml and 0.08±0.01 ng/ml, P<0.001). After dialysis, the concentrations decreased significantly, (0.21±0.02 ng/ml, P<0.001). However the 8-OHdG concentrations after dialysis were still significantly higher compared with concentrations of the control group (Table 2). The significant individual decrease pre- and post-dialysis for non-diabetic and diabetic HD patients are shown in FIG. 1C (P<0.001, P=0.018). There was a significant correlation between increased plasma 8-OHdG concentration and decreased selenium concentration in diabetic HD patients pre-dialysis treatment, P=0.004 (FIG. 4).

Except for the correlation between deceased selenium and increased 8-OHdG in diabetic HD patients (FIG. 4), there was no significant correlation between any other trace elements found in HD patients or controls and markers for AGE, inflammation and oxidative stress (data not shown). In addition there were no differences between trace element distribution in plasma or whole blood between HD patients and control group (data not shown). All control values were in good agreement with the standard range of trace element concentration [6]. All analysed effluent samples taken post-dialysis from the HD patients showed small quantities of trace elements, neglectable compared with the concentrations found in plasma or blood of control or HD patients (data not shown).

It is well recognized that HD patients are at elevated risk of inflammation and oxidative stress, resulting in endothelial dysfunction, atherosclerosis and CVD [13, 14, 18]. Accumulation and deficiency of trace elements in HD patients have also been reported by several studies [1, 14, 16, 17]. In HD patients with diabetes this risk is increased even further due to AGE formation and co-morbidity [1]. Abnormal glutathione metabolism, inflammation and increased cytotoxicity are seen in endothelial cells exposed to glucose-induced oxidative stress [18, 19].

In the study described herein, the lowest levels of selenium were found in the diabetic HD patients. Low concentrations of selenium could lead to increased oxidative stress and inflammation. Indeed, our study supports this hypothesis by finding a significant correlation between plasma selenium concentration and concentration of 8-OHdG, thus illustrating that a drop in selenium concentration leads to increased 8-OHdG concentrations. Additionally, we observed increased PTX-3 levels and decreased 8-OHdG levels during dialysis treatment in all HD patients suggesting that PTX-3 is rapidly formed during dialysis, but not removed by the treatment. Previous studies, using in-deepened filter, have shown a peak of PTX-3 180 min after start of the HD session. This might explain why we observed lower PTX-3 concentrations than Sjoberg et al [4]. Pentosidine is recognized as age-related marker for diabetic complications [20, 21], which could affect the plasma pentosidine status in the present study.

There is a weakness in the study design as the age differences between the HD patients (mean 67) and the controls (mean 23). Therefore it is very surprising that it was found that higher pentosidine concentrations in plasma from HD patients without diabetes compared to HD patients with diabetes. A probable explanation could be that the diabetic group is under strict metabolic control and insulin-treated, which could explain the reduced AGE formation [3].

Selenium is located in the active site of glutathione peroxidase, reducing oxidative stress by transformation of hydrogen peroxide to water. Aging can contribute to reduced selenium status [9]. However, our results are not only age related since we observed a significantly higher selenium deficiency in our diabetic HD group compared to the non-diabetic patients. Copper deficiency has been associated with cardiovascular disease (CVD), but uremia leads to copper accumulation [22] and elevated levels of copper are associated with oxidative stress in diabetic patients [19]. We observed higher concentrations of copper in HD patients compared with controls, but due to the dual properties of this ion any conclusion of the impact of this finding is difficult. Zinc, as a part of Zn—Cu superoxide dismutase, is an important antioxidant, but this ion is also involved in the sense of smell and taste, which, in turn, is correlated to malnutrition [8, 13, 16]. Long-term HD patients often exhibit protein-energy malnutrition (PEM) in combination with inflammation, the so-called malnutrition-inflammation complex syndrome (MICS), suggesting that the two events often co-exist, leading to increased atherosclerosis, hospitalization and mortality [2, 11, 12, 16]. Elevated levels of essential zinc-containing metalloenzymes, which reversibly convert and transport water and carbon dioxide to bicarbonate, are observed in erythrocytes of renal failure patients, making the zinc ions not able to freely equilibrate with the plasma. Hsieh et al. showed low to normal long-term plasma zinc deficiency in their study population over time, to compare with our finding of a ten-fold increase of zinc in our whole blood samples compared to plasma. As zinc accumulates in bone, and also possibly in erythrocytes of uremic patients, potential plasma deficiency needs further investigation [2, 6, 7]. Rubidium deficiency is connected to protein malnutrition and inflammation [6, 23]. However, the plasma deficiency tends to decrease after dialysis treatment, as our study also confirmed, suggesting that the deficiency in uremic patients is not only due to malnutrition [23]. However, it is verified by the study that rubidium is mostly located in erythrocytes and not in plasma [24].

As previously shown, it is confirmed that chromium concentrations are higher in HD patients compared with healthy controls [10]. Chromium is more abundant in elderly patients and less abundant in diabetes patients, probably related to its actions on glucose metabolism [25]. Our study is in good agreement with these reports, as we found the highest chromium levels in the older HD patients compared with the younger controls, and higher levels in non-diabetic HD patients compared with diabetic HD patients. Manganese deficiency is not a recognized problem in humans and the reports are conflicting regarding plasma accumulation [1, 12]; however, it is known that accumulation of manganese in the brain of dialysis patients can cause motor dysfunction [29]. The results indicate an increased manganese concentration post-dialysis and a significantly higher manganese concentration in HD patients compared to controls.

Although cobalt levels are rarely investigated in HD patients, cobalt deficiency is identified as a risk [10]. Cobalt is a part of the essential vitamin $B_{12}$ (Cobalamin) and is thus involved in the regulation of central nervous system and in the synthesis of erythrocytes. Deficiency can lead to anemia and neurological symptoms due to inhibition of DNA synthesis [10]. Compared with controls, the HD patients had higher cobalt concentrations and no deficiency could be detected. The concentration of cobalt was slightly increasing during dialysis in our study and the majority of this ion could be found in plasma.

The increased levels of inflammatory- and oxidative stress-markers and the altered concentrations of trace elements in all HD patients compared with controls support focus on at least monitoring of the trace elements to improve the inflammatory and oxidative status in these patients. The complexity of trace element distribution between plasma and whole blood in all groups and the observed altered concentrations of trace elements during dialysis need to be further investigated. Some changes during dialysis treatment could simply be explained by possible removal during ultra filtration or increased concentrations due to fluid removal from the patient.

Today there are no available trace element-containing dialysis fluids on the market; however, instead of current supplementation, such as oral and intravenous, adding selective trace elements in suitable concentrations to the dialysis fluid would ensure correct plasma concentrations due to the equilibrium across the dialysis membrane.

FIGURE LEGENDS

Figure 2:
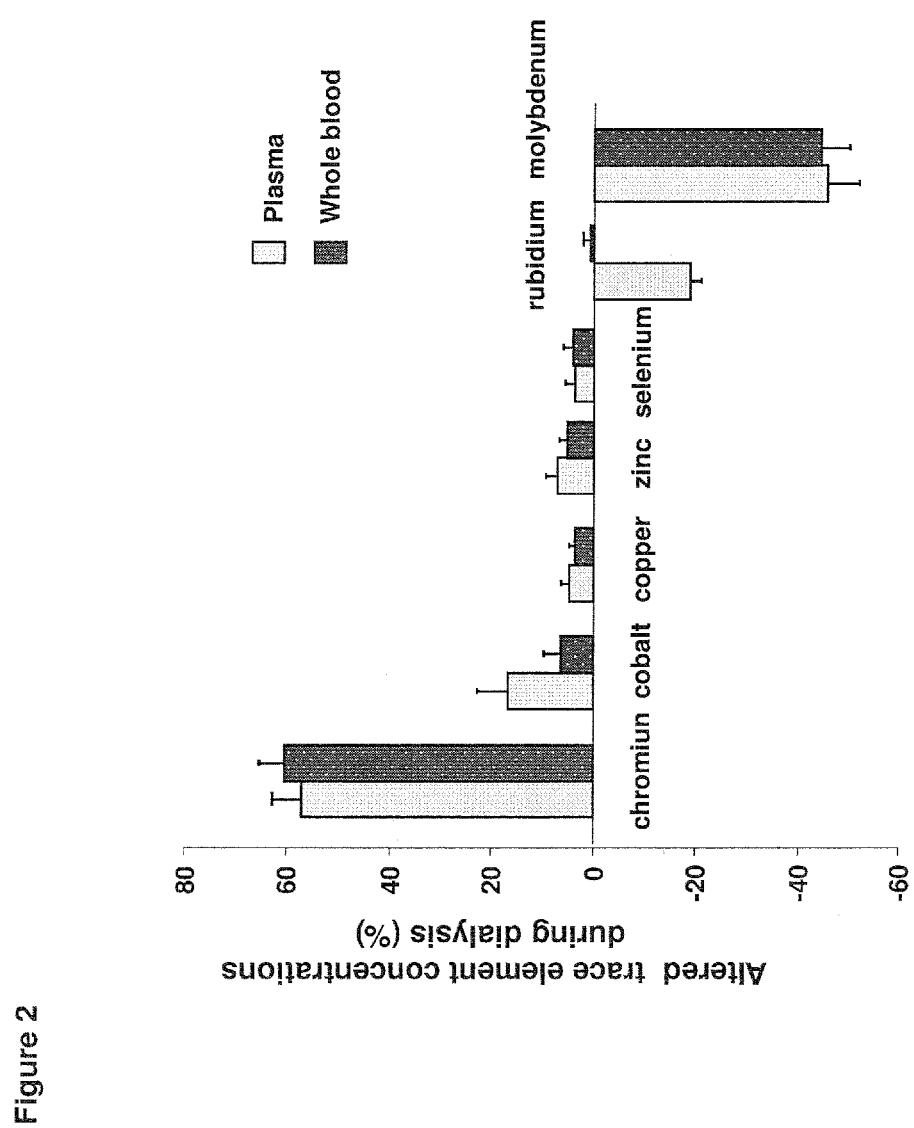
FIG. 2 shows the altered trace element concentrations during dialysis (%).

FIG. 1: Altered concentrations of trace elements in HD patients Plasma and whole blood concentrations of trace elements chromium (A), manganese (B), cobalt (C), copper (D), zinc (E), selenium (F), rubidium (G) and molybdenum (H) in healthy controls (white bars P, B) and non-diabetic HD patients (striped bars) and diabetic HD patients (grey bars). Pre-(P1, B1) and post-(P2, B2) dialysis values of plasma and whole blood. (A) Chromium showed significant higher concentration both in non- and diabetic HD patients compared to controls and a significant increase during treatment in both HD groups. There was also a significant higher plasma concentration post-dialysis in non-diabetic HD patients compared to diabetic HD patients. (B) Manganese was mainly found in whole blood and was significant lower in controls than in the all HD patients. Manganese was significantly increasing in whole blood samples over dialysis in both HD groups.

(C) Plasma concentration of cobalt was significantly increased in both HD groups compared to controls. (D) Copper was mostly detected in plasma and was significantly increased in diabetic HD patients compared to controls. (E) Zinc was mostly found in whole blood and it was more abundant in non-diabetic dialysis patients than in diabetic HD patients compared to controls. (F) Lower selenium concentrations were seen in both plasma and whole blood of both HD groups compared to controls. There was a significant difference between the two groups of HD patients, where the diabetic group had lower concentrations both in plasma and whole blood. The diabetic HD patients also showed significant increase of selenium in whole blood during dialysis. (G) Rubidium concentrations were significantly lower in whole blood of both HD groups compared with the control group, but there were no differences between the HD groups. (H) Compared with controls, both HD groups had higher concentrations of molybdenum. The concentration of molybdenum was the highest in plasma of the diabetic group pre-dialysis compared to non-diabetic and significantly reduced during dialysis in both HD groups.

All samples are shown as mean values±SEM, n=48-50 controls, 27-31 non-diabetic HD patients and 15-17 diabetic HD patients, a=*$P<0.001$, b=$P<0.01$, c=*$P<0.05$ FIG. 2: Plasma and whole blood concentrations of trace elements during dialysis.

Percentage differences in plasma and whole blood concentrations of trace elements chromium, cobalt, copper, zinc, selenium, rubidium and molybdenum during an HD treatment are shown. Concentrations of chromium, cobalt, copper and zinc are elevated post-treatment in both plasma and whole blood, while concentrations of rubidium and molybdenum were lower after treatment.

All samples are shown as mean values±SEM, n=44-47

Figure 3:
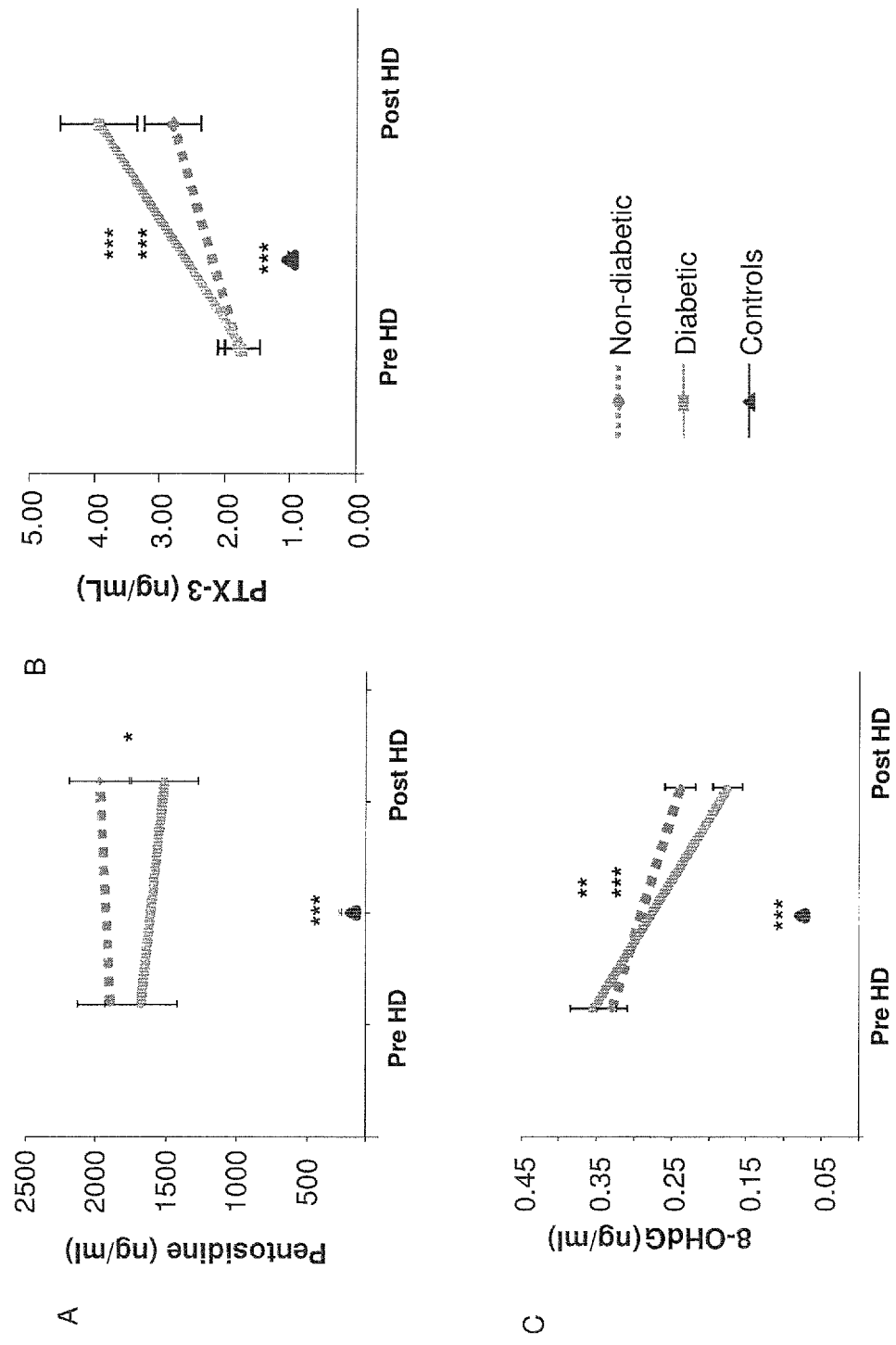
FIG. 3 A-C shows the levels of advanced glycation end products (AGE) marker for acute inflammation and markers for oxidative stress pre- and post-a dialysis treatment, compared with a group of healthy subjects (pentosidine.

FIG. 3: Markers for AGE formation, inflammation and oxidative stress in non-diabetic and diabetic HD patients compared to healthy controls (A).

Pentosidine concentrations were significantly higher in non-diabetic HD patients' post-dialysis compared to diabetic HD patients. Both HD groups had significantly elevated pentosidine concentrations compared to controls. (B) Significantly increased plasma PTX-3 concentrations were measured between non-diabetic and diabetic patients HD patients compared to control, both pre- and post-dialysis. Both HD groups also had a significant increased PTX-3 concentration during dialysis. (C) The levels of 8-OHdG decreased significantly during dialysis in both diabetic and non-diabetic HD patients. The values of 8-OHdG in both HD patient groups were significantly higher than the control values.

All samples are shown as mean values±SEM of 24 non-diabetic, 16 diabetic HD-patients and 51 controls. *$P<0.05$, $P<0.01$, *$P<0.001$ FIG. 4: Correlation between selenium and 8-OHdG in diabetic HD patients is shown. A negative correlation between the plasma selenium concentration and the plasma 8-OHdG concentration pre-dialysis treatment was observed, P=0.0044. All samples are shown as mean values, n=15

Figure 5:
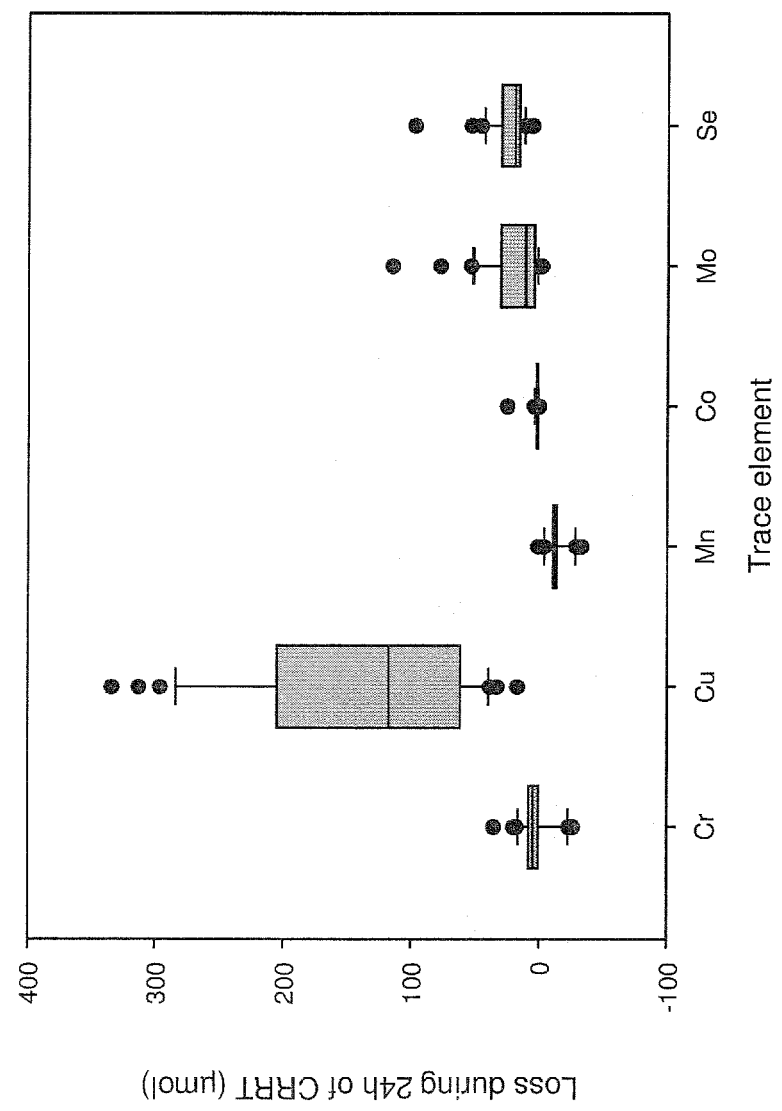
FIG. 5A shows the loss of trace elements (Cr, Cu, Mn, Co, Mo, Se) during 24 h in patients with CRRT treatment (acute dialysis treatment).
FIG. 5B shows the loss of trace elements (Zn, Ru) during 24 h in patients with CRRT treatment (acute dialysis treatment).
FIG. 5C shows the loss of trace elements (Cr, Mn, Co, Se) during 4 h in patients with hemodialysis (HD) treatment (chronic dialysis treatment).
FIG. 5D shows the loss of trace elements (Cu, Zn) during 4 h in patients with hemodialysis treatment (chronic dialysis treatment).
FIG. 5E shows the loss of trace elements (Rb) during 24 h in patients with hemodialysis treatment (chronic dialysis treatment).
Figure 5:
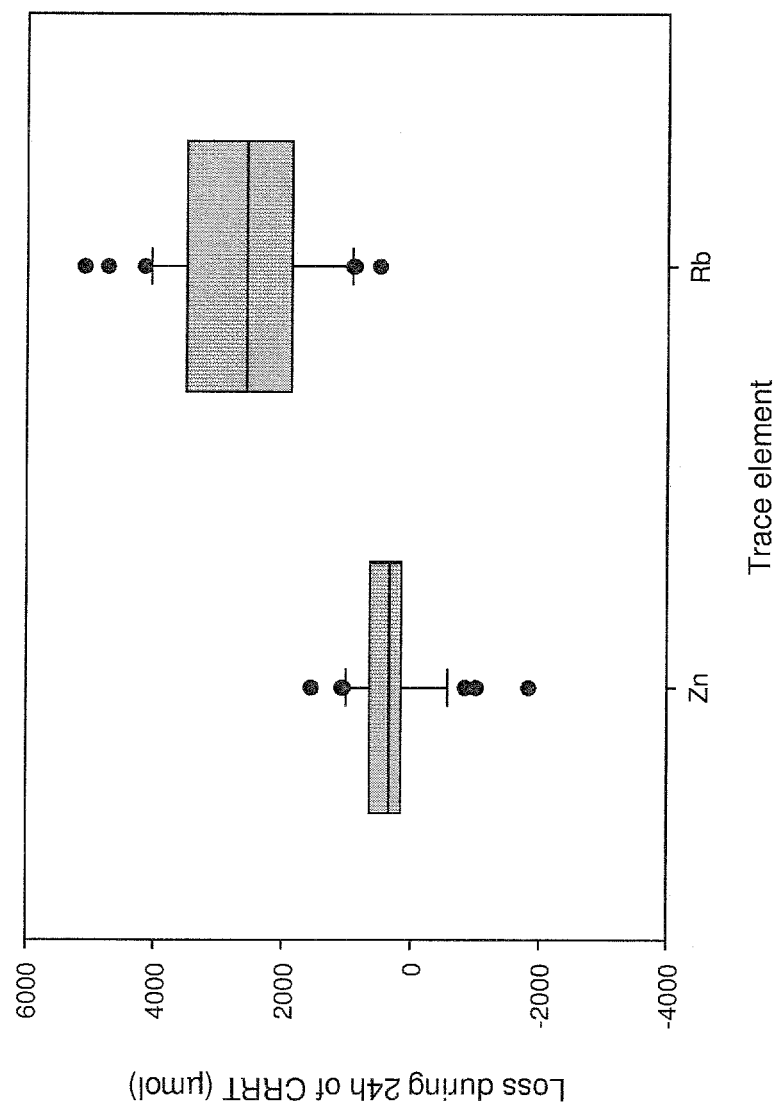
Figure 5:
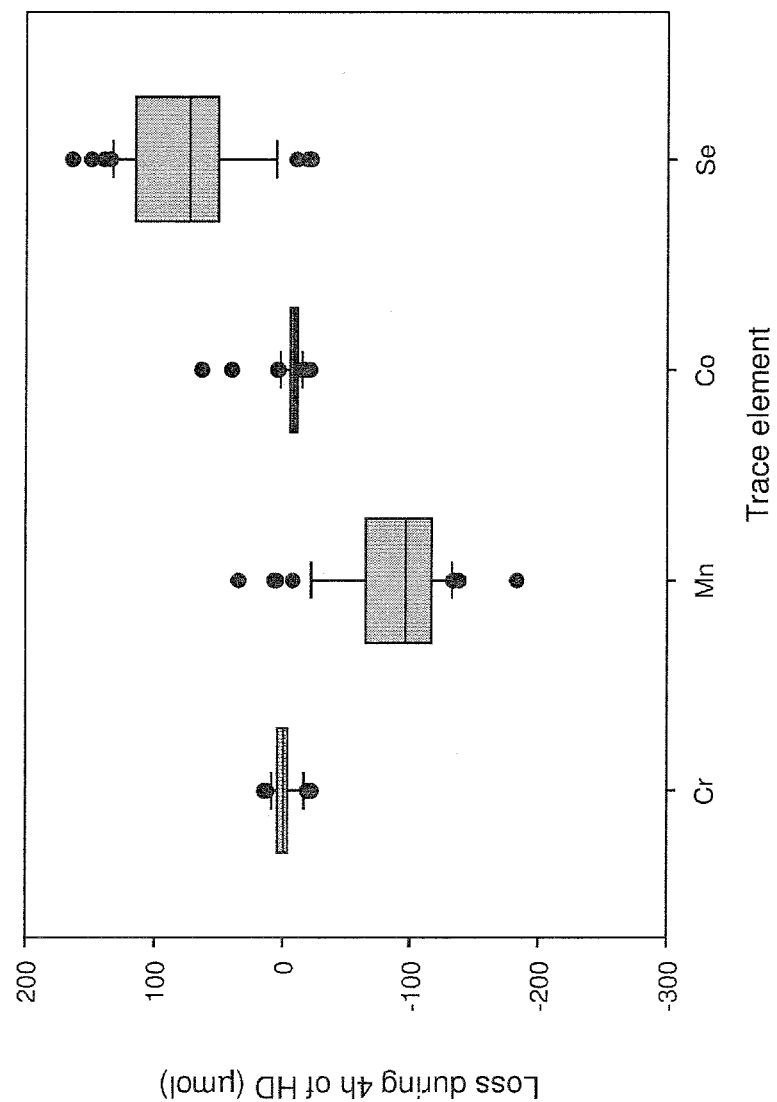
Figure 5:
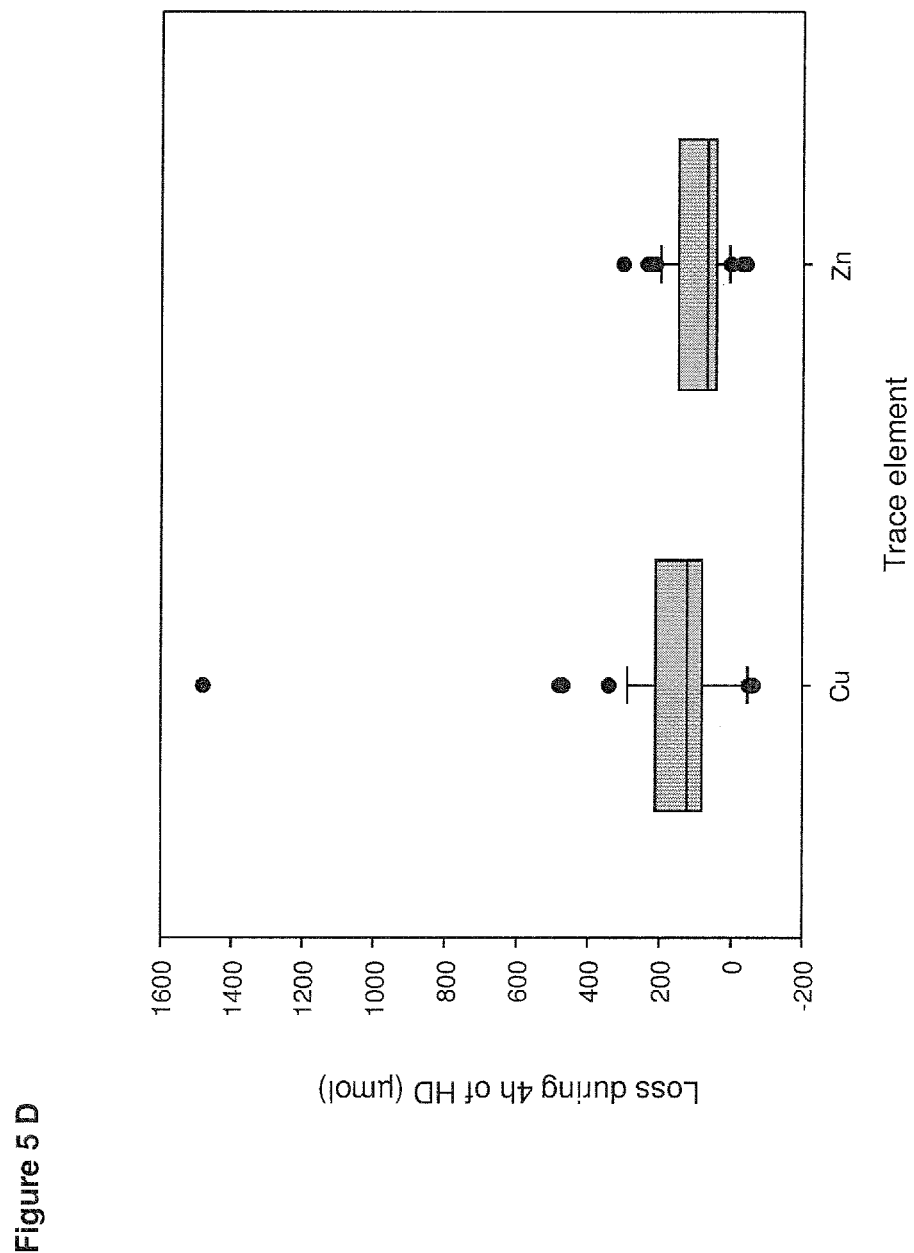
Figure 5:
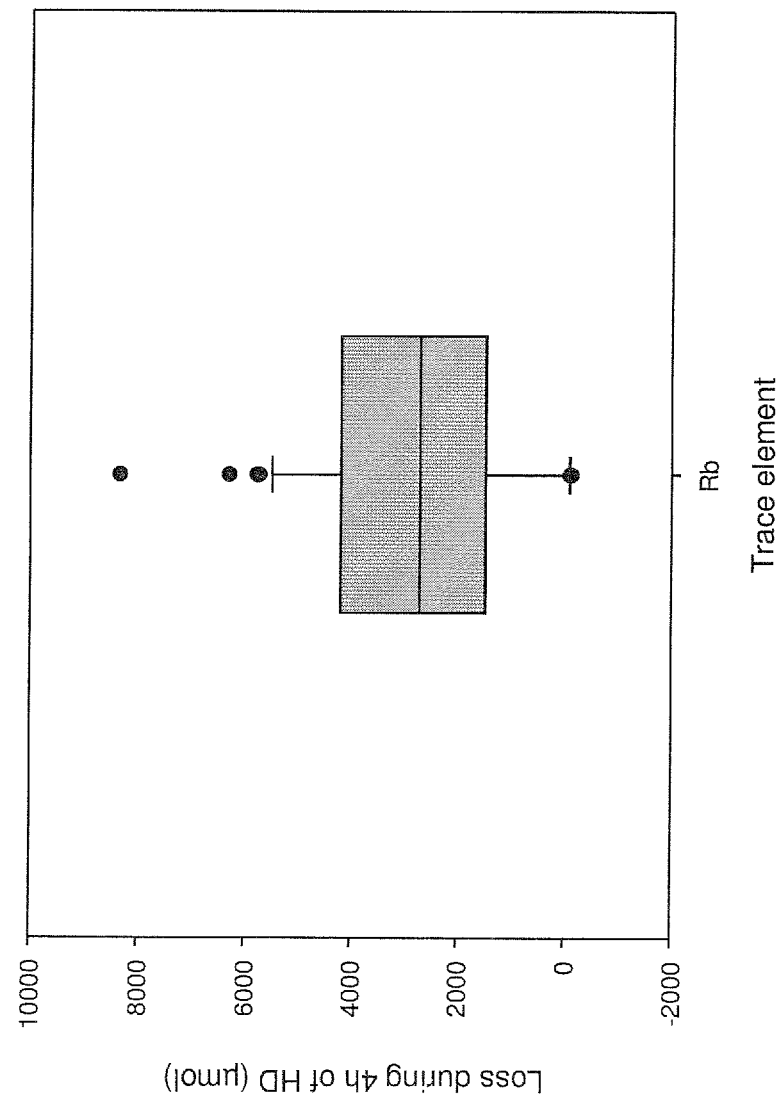

FIG. 5A: The actual loss of chromium, copper, manganese, cobalt, molybdenum, and selenium during 24 hours of CRRT is shown. A significant loss of the trace elements during dialysis is shown.

FIG. 5B: Show the actual loss of zinc and rubidium and some subjects show a uptake of zinc (negative loss) while others show loss of zinc during 24 hours of CRRT. All patients in the study had a large loss of rubidium during the treatment.

FIG. 5C: Show the actual loss of chromium, manganese cobalt, and selenium. There were a significant removal of selenium in most patients during 4 hours of HD treatment, despite a rather low plasma concentration of selenium (not shown), while there are no manganese removal at all but rather an uptake of the small amounts found in the dialysis and replacement fluid.

FIG. 5D: The actual removal of copper and zinc from HD patients is shown. There were a removal of those trace elements in a majority of the patients in this group of patients.

FIG. 5E: Show the loss of rubidium in HD patients and there were a significant removal of rubidium in a majority of the patients in the present study.

TABLE 1

P1 = plasma sample pre-dialysis P2 = plasma sample post-dialysis B1 = Whole blood sample pre-dialysis B2 = whole blood sample post-dialysis, all samples are shown as mean ± Std error of mean, (SEM), n = 44-50

|    | P1 (μg/l) ± SEM | P2 (μg/l) ± SEM | P control (μg/l) ± SEM | B1 (μg/l) ± SEM | B2 (μg/l) ± SEM | B control (μg/l) ± SEM |
|----|---|---|---|---|---|---|
| Cr | 3.3 ± 0.3 | 5.2 ± 0.6 | 0.3 ± 0.02 | 2.1 ± 0.2 | 3.4 ± 0.4 | 0.3 ± 0.02 |
| Mn | 0.8 ± 0.03 | 3.4 ± 0.9 | 0.7 ± 0.02 | 17.0 ± 1.1 | 19.3 ± 1.4 | 9.2 ± 0.4 |
| Co | 0.6 ± 0.03 | 0.6 ± 0.1 | 0.4 ± 0.02 | 0.5 ± 0.02 | 0.5 ± 0.03 | 0.3 ± 0.01 |
| Cu | 1113 ± 33 | 1178 ± 29 | 1059 ± 45 | 855 ± 18 | 882 ± 17 | 861 ± 27 |
| Zn | 644 ± 13 | 685 ± 17 | 719 ± 17 | 5610 ± 138 | 5842 ± 131 | 5189 ± 124 |
| Se | 53 ± 2 | 55 ± 2 | 81 ± 1.9 | 66 ± 2 | 68 ± 2 | 102 ± 3 |
| Rb | 187 ± 5 | 150 ± 4 | 271 ± 5 | 972 ± 30 | 974 ± 30 | 1966 ± 51 |
| Mo | 2.6 ± 0.2 | 1.3 ± 0.1 | 0.8 ± 0.1 | 2.0 ± 0.2 | 1.0 ± 0.1 | 0.6 ± 0.1 |

TABLE 2

Pre- (P1) and post- (P2) dialysis plasma concentrations of pentosidine, PTX-3 and 8-OHdG in all HD patients compared to controls

|  | P1 (ng/ml) ± SEM | P2 (ng/ml) ± SEM | Control ± SEM |
|---|---|---|---|
| Pentosidine | 1805 ± 172 | 1780 ± 163 | 177 ± 8 |
| PTX-3 | 1.8 ± 0.2 | 3.3 ± 0.4 | 0.7 ± 0.04 |
| 8-OHdG | 0.34 ± 0.02 | 0.21 ± 0.02 | 0.08 ± 0.01 |

All samples are shown as mean ± SD error of mean (SEM), n = 38-51.

TABLE 3

Demographic data of HD patients and healthy controls

|  | Non-diabetic | Diabetic | Controls |
|---|---|---|---|
| Diabetes nephropathy |  | 15 |  |
| Nephroangiosclerosis or hypertensive nephropathy | 11 | 1 |  |
| Glomerulonephritis | 7 |  |  |
| Hereditary or intersitial nephritis | 4 |  |  |
| Other or unknown diagnosis | 12 | 1 |  |
| Number of subjects | 30 | 17 | 51 |
| Age, years (25th-75th percentile) | 62.5 (79.75-77.5)* | 72 (58-76.5)* | 22 (22-24) |
| Gender female/male | 12/5 | 22/8 | 20/31 |
| Time on dialysis, months (25th-75th percentile) | 57 (20.75-97.5) | 31 (13.5-55.5) | N/A |

(*significant vs. controls, P < 0.001)

While the invention has been described in connection with what is presently considered to be the most practical embodiments, it is to be understood that the invention is not to be limited to the disclosed embodiments, but on the contrary, is intended to cover various modifications and equivalents included within the spirit and the scope of the appended claims.

REFERENCES

1. Dursun, B., et al., *Are uremia, diabetes, and atherosclerosis linked with impaired antioxidant mechanisms?* J Investig Med, 2008. 56(2): p. 545-52.
2. Kalantar-Zadeh, K., et al., *Malnutrition-inflammation complex syndrome in dialysis patients: causes and consequences.* Am J Kidney Dis, 2003. 42(5): p. 864-81.
3. Lapolla, A., et al., *Pentosidine plasma levels and relation with metabolic control in diabetic patients.* Horm Metab Res, 2005. 37(4): p. 252-6.
4. Sjoberg, B., et al., *Pentraxin 3, a Sensitive Early Marker of Hemodialysis-Induced Inflammation.* Blood Purif, 2012. 34(3-4): p. 290-297.
5. Wu, L. L., et al., *Urinary 8-OHdG: a marker of oxidative stress to DNA and a risk factor for cancer, atherosclerosis and diabetics.* Clin Chim Acta, 2004. 339(1-2): p. 1-9.
6. Zima, T., et al., *Trace elements in end-stage renal disease. 2. Clinical implication of trace elements.* Blood Purif, 1999. 17(4): p. 187-98.
7. Hsieh, Y. Y., et al., *Long-term changes in trace elements in patients undergoing chronic hemodialysis.* Biol Trace Elem Res, 2006. 109(2): p. 115-21.
8. Faure, P., et al., *Selenium supplementation decreases nuclear factor-kappa B activity in peripheral blood mononuclear cells from type 2 diabetic patients.* Eur J Clin Invest, 2004. 34(7): p. 475-81.
9. Boosalis, M. G., *The role of selenium in chronic disease.* Nutr Clin Pract, 2008. 23(2): p. 152-60.
10. Tonelli, M., et al., *Trace elements in hemodialysis patients: a systematic review and meta-analysis.* BMC Med, 2009. 7: p. 25.
11. Ciechanover, M., et al., *Malrecognition of taste in uremia.* Nephron, 1980. 26(1): p. 20-2.
12. Mekki, K., et al., *Hemodialysis duration impairs food intake and nutritional parameters in chronic kidney disease patients.* Int Urol Nephrol, 2010. 44(1): p. 237-44.
13. Lynch, K. E., et al., *Altered Taste Perception and Nutritional Status Among Hemodialysis Patients.* J Ren Nutr, 2012.
14. Druml, W. and H. P. Kierdorf, *Parenteral nutrition in patients with renal failure—Guidelines on Parenteral Nutrition, Chapter 17.* Ger Med Sci, 2009. 7: p. Doc11.
15. Barany, E., Bergdahl, I. A., Schütz, A., Skerfving, S., Oskarsson, A., *Inductively coupled plasma mass spectrometry for direct multi-element analysis of diluted human blood and serum.* J. Anal. Atomic Spectrometry, 1997. 12: p. 1005-9.
16. Rucker, D., R. Thadhani, and M. Tonelli, *Trace Element Status in Hemodialysis Patients.* Seminars in Dialysis, 2010. 23(4): p. 389-395.
17. Marques de Mattos, A., et al., *Protein oxidative stress and dyslipidemia in dialysis patients.* Ther Apher Dial, 2012. 16(1): p. 68-74.
18. Bryland, A., et al., *Citrate treatment reduces endothelial death and inflammation under hyperglycaemic conditions.* Diab Vasc Dis Res, 2011. 9(1): p. 42-51.
19. Tanaka, A., et al., *Role of copper ion in the pathogenesis of type 2 diabetes.* Endocr J, 2009. 56(5): p. 699-706.
20. Morales, S., J. A. Garcia-Salcedo, and M. Munoz-Torres, *[Pentosidine: a new biomarker in diabetes mellitus complications].* Med Clin (Barc), 2011. 136(7): p. 298-302.
21. Kashiwagi, A., et al., *Abnormal glutathione metabolism and increased cytotoxicity caused by H2O2 in human umbilical vein endothelial cells cultured in high glucose medium.* Diabetologia, 1994. 37(3): p. 264-9.
22. Vanholder, R., et al., *The role of trace elements in uraemic toxicity.* Nephrol Dial Transplant, 2002. 17 Suppl 2: p. 2-8.
23. Canavese, C., et al., *Rubidium, salami and depression. You cannot have everything in life.* Blood Purif, 2008. 26(4): p. 311-4.
24. Relman, A. S., *The physiological behavior of rubidium and cesium in relation to that of potassium.* Yale J Biol Med, 1956. 29(3): p. 248-62.
25. Cefalu, W. T. and F. B. Hu, *Role of chromium in human health and in diabetes.* Diabetes Care, 2004. 27(11): p. 2741-51.
26. Sprenger, K. B., et al., *Improvement of uremic neuropathy and hypogeusia by dialysate zinc supplementation: a double-blind study.* Kidney Int Suppl, 1983. 16: p. S315-8.

Further Aspects of the Invention:

An aspect of the invention is a composition comprising selenium (Se); with the proviso that the said composition is essentially free of one or more of the trace elements selected from chromium (Cr), manganese (Mn), and copper (Cu).

A second aspect of the invention is a composition as above which then further comprises one or more trace elements selected from the group of cobalt (Co), molybdenum (Mo), zinc (Zn), A third aspect of the invention is a composition according to any of first or second aspect wherein said composition contains 0.6-1.8 µM of selenium (Se), preferably 1-1.5 µM of selenium.

A fourth aspect of the invention is a composition according to any of first to third aspect wherein selenium is in form of selenite (SeO$_3^2$×H2O).

A fifth aspect of the invention is a composition according to any of first to fourth aspect which further comprises rubidium (Rb).

A sixth aspect of the invention is a composition according to fifth aspect wherein the composition contains between 0.1-2.7 µM rubidium (Rb), preferably between 1.4-2.7 µM rubidium (Rb), more preferably 1.6-2.5 µM rubidium.

A seventh aspect of the invention is a composition according to any of first to sixth aspect wherein the composition is a treatment fluid.

An eighth aspect of the invention is a composition according to any of first to seventh aspect wherein said composition is dialysis fluid.

A ninth aspect of the invention is a composition according to any of first to seventh aspect wherein said composition is replacement fluid.

A tenth aspect of the invention is a composition according to any of first to sixth aspect wherein the composition is a peritoneal dialysis fluid.

An eleventh aspect of the invention is the use of the composition, as defined in any of first to sixth aspect, in dialysis treatment of diabetic patient.

A twelfth aspect of the invention is a composition as defined in any of first to sixth aspect comprising selenium (Se) for dialysis treatment.

A thirteenth aspect of the invention is a composition according to twelfth aspect wherein said dialysis treatment is intermittent dialysis treatment.

A fourteenth aspect of the invention is a composition according to twelfth aspect, wherein said dialysis treatment is continuous dialysis treatment.

A fifteenth aspect of the invention is a composition according to twelfth aspect, wherein said dialysis treatment is peritoneal dialysis treatment.

A sixteenth aspect of the invention is selenium for use in dialysis therapy.

A seventeenth aspect of the present invention is the use of selenium for the manufacturing of a medicament for treatment or prevention of selenium deficiency in connection with dialysis therapy.

An eighteenth aspect of the present invention is the use of selenium in accordance with seventeenth aspect, with the proviso that the medicament is essential free from one or more of chromium (Cr), manganese (Mn), or copper (Cu).

A nineteenth aspect of the present invention is the use of selenium in accordance with seventeenth aspect, wherein the medicament further comprises rubidium (Rb).

A twentieth aspect of the invention is a citrate containing formulation comprising the trace element selenium (Se).

A twenty first aspect of the invention is a citrate containing formulation according to twentieth aspect which further comprises one or more trace elements selected from the group of cobalt (Co), molybdenum (Mb), and zinc (Zn).

A twenty second aspect of the invention is a citrate containing formulation according to twentieth and twenty first aspects wherein the formulation contains 0.6-1.8 µM of selenium, preferably 1.0-1.6 µM of selenium.

A twenty third aspect of the invention is a citrate containing formulation according to any of twentieth to twenty second aspects wherein selenium is in form of selenite (SeO$_3^{2-}$).

A twenty fourth aspect of the invention is a citrate containing formulation according to any of twentieth to twenty fourth aspect which further comprises rubidium (Rb).

A twenty fifth aspect of the invention is a citrate containing formulation according to twenty fourth aspect wherein the formulation contains between 0.1 and 4.2 µM rubidium (Rb), preferably between 1.4 and 4.2 µM rubidium (Rb), more preferably between 1.6 and 2.5 µM.

A twenty sixth aspect of the invention is a citrate containing formulation according to any of twentieth to twenty fifth aspect wherein the formulation is essentially free from one or more of chromium (Cr), manganese (Mn), and copper (Cu).

A twenty seventh aspect of the invention is a citrate containing formulation according to any of twentieth to twenty sixth aspect wherein the formulation is a treatment fluid.

A twenty eighth aspect of the invention is a citrate containing formulation according to any of twentieth to twenty sixth aspect wherein the formulation is an anticoagulation fluid.

A twenty ninth aspect of the invention is a citrate containing formulation according to any of twentieth to twenty sixth aspect wherein the formulation is a peritoneal dialysis fluid.

A thirtieth aspect of the invention is a citrate containing formulation as defined in any of twentieth to twenty sixth aspect for dialysis treatment.

A thirty first aspect of the invention is a citrate containing formulation according to any of claims twentieth to twenty sixth aspect wherein the formulation is for intermittent dialysis treatment.

A thirty second aspect of the invention is a citrate containing formulation according to any of twentieth to twenty sixth aspect wherein the composition is for continuous dialysis treatment.

A thirty third aspect of the invention is a citrate containing formulation according to any of twentieth to twenty sixth aspect wherein the composition is for peritoneal dialysis treatment.

A thirty fourth aspect of the invention is the use of a citrate containing formulation as defined in any of twentieth to twenty sixth aspect in dialysis treatment of diabetic patient.

A thirty fifth aspect of the invention is the use of selenium for the manufacturing of a medicament for treatment or prevention of selenium deficiency in connection with dialysis therapy.

A thirty sixth aspect of the invention is the use according to any the thirty fourth and thirty fifth aspects wherein the medicament is a composition for dialysis treatment.

The invention claimed is:

1. A dialysis formulation comprising:
   selenium (Se) in a concentration of 0.5-2.5 µM; and
   rubidium (Rb) in a concentration of 0.1-4.7 µM, the dialysis formulation being essentially free of one or more of the trace elements selected from chromium (Cr), manganese (Mn) and copper (Cu).

2. A dialysis formulation according to claim 1, wherein the dialysis formulation is a citrate containing formulation.

3. A dialysis formulation according to claim 1, wherein the dialysis formulation further comprises one or more trace elements selected from the group of cobalt (Co), molybdenum (Mo), and zinc (Zn).

4. A dialysis formulation according to claim 1, wherein selenium is in form of selenite.

5. The dialysis formulation of claim 1 comprising 0.6-1.8 µM of selenium.

6. The dialysis formulation of claim 1 comprising 1-1.5 µM of selenium.

7. The dialysis formulation of claim 1 comprising 1.4-4.2 µM of rubidium.

8. The dialysis formulation of claim 1 comprising 1.6-2.5 µM of rubidium.

9. A method of performing a dialysis therapy, the method comprising use of the dialysis formulation as defined in claim 1.

* * * * *